US010441953B2

(12) United States Patent
Thomsen et al.

(10) Patent No.: US 10,441,953 B2
(45) Date of Patent: Oct. 15, 2019

(54) DEVICE AND METHOD FOR HEATING A FLUID CHAMBER

(71) Applicant: Biovices IPR Holdings A/S, Copenhagen (DK)

(72) Inventors: Lars Thomsen, Hong Kong (HK); Soiwasa Soikum, Sri Ayutthaya (TH)

(73) Assignee: Biovices IPR Holdings A/S, copenhagen (DK)

( * ) Notice: Subject to any disclaimer, the term of this patent is extended or adjusted under 35 U.S.C. 154(b) by 507 days.

(21) Appl. No.: 15/035,353

(22) PCT Filed: Nov. 10, 2014

(86) PCT No.: PCT/IB2014/002622
§ 371 (c)(1),
(2) Date: May 9, 2016

(87) PCT Pub. No.: WO2015/068038
PCT Pub. Date: May 14, 2015

(65) Prior Publication Data
US 2016/0332164 A1    Nov. 17, 2016

(30) Foreign Application Priority Data

Nov. 8, 2013 (GB) .................................. 1319759.5

(51) Int. Cl.
*B01L 7/00* (2006.01)
*C12Q 1/686* (2018.01)

(52) U.S. Cl.
CPC .............. *B01L 7/52* (2013.01); *C12Q 1/686* (2013.01); *B01L 2200/142* (2013.01);
(Continued)

(58) Field of Classification Search
None
See application file for complete search history.

(56) References Cited

U.S. PATENT DOCUMENTS 5,281,516 A * 1/1994 Stapleton .................. B01L 7/52
165/61
5,602,756 A * 2/1997 Atwood .............. B01L 3/50851
165/205

(Continued)

*Primary Examiner* — Jill A Warden
*Assistant Examiner* — Brittany I Fisher
(74) *Attorney, Agent, or Firm* — Stradley Ronon Stevens & Young

(57) ABSTRACT

The present invention relates to an apparatus, system and method for heating a fluid chamber. Devices for heating a fluid chamber, in which a temperature sensitive or temperature-initiated chemical reaction takes place, typically comprise a heater and a temperature sensor. A heater device heats a fluid container which is separable from the heater device. The device comprises one or more substrates each forming a surface of a receiving location for the fluid container. A first heater is disposed on a surface of a substrate in thermal communication with a first heat transfer surface within the receiving location. A second heater is disposed on a surface of a substrate in thermal communication with a second heat transfer surface and is spaced apart from the first heat transfer surface. A first temperature sensor is in thermal communication with the first heater and a second temperature sensor is in thermal communication with the second heater. The device is configured to conform to the shape of the fluid container such that the first and the second heat transfer surfaces come into contact with the fluid container.

19 Claims, 17 Drawing Sheets

(52) U.S. Cl.
CPC ... *B01L 2200/147* (2013.01); *B01L 2300/021* (2013.01); *B01L 2300/041* (2013.01); *B01L 2300/0609* (2013.01); *B01L 2300/0858* (2013.01); *B01L 2300/123* (2013.01); *B01L 2300/1827* (2013.01); *B01L 2300/1844* (2013.01); *B01L 2300/1894* (2013.01)

(56) References Cited

U.S. PATENT DOCUMENTS

| | | | | |
|---|---|---|---|---|
| 5,616,301 A | * | 4/1997 | Moser | B01L 7/52 422/562 |
| 5,626,301 A | * | 5/1997 | Morikawa | B23D 17/00 241/101.73 |
| 5,720,406 A | * | 2/1998 | Fassbind | B01L 3/5085 220/23.4 |
| 5,935,524 A | * | 8/1999 | Bass | B01L 9/06 422/52 |
| 6,004,513 A | * | 12/1999 | Albagli | B01L 7/52 422/68.1 |
| 6,060,022 A | * | 5/2000 | Pang | G01N 35/0095 422/63 |
| 6,197,572 B1 | * | 3/2001 | Schneebeli | B01L 3/50851 435/286.2 |
| 6,403,037 B1 | * | 6/2002 | Chang | B01L 3/502 250/238 |
| 6,472,186 B1 | * | 10/2002 | Quintanar | C12Q 1/6851 435/183 |
| 6,519,032 B1 | * | 2/2003 | Kuebler | B01D 15/08 356/246 |
| 6,555,792 B1 | * | 4/2003 | Elsener | B01J 19/0093 219/428 |
| 6,638,761 B2 | * | 10/2003 | Shin | B01L 3/5085 219/385 |
| 6,677,151 B2 | * | 1/2004 | Sandell | B01L 7/52 435/287.2 |
| 7,049,558 B2 | * | 5/2006 | Baer | B01J 19/0093 219/548 |
| 7,081,600 B2 | * | 7/2006 | Brown | B01L 3/50851 219/385 |
| 7,133,726 B1 | * | 11/2006 | Atwood | B01L 7/52 700/1 |
| 7,892,504 B2 | * | 2/2011 | Taike | B01L 3/50855 206/565 |
| 2002/0072112 A1 | * | 6/2002 | Atwood | B01L 3/50851 435/303.1 |
| 2004/0110301 A1 | * | 6/2004 | Neilson | G01N 25/482 436/34 |
| 2007/0196237 A1 | * | 8/2007 | Neuzil | B01L 3/50851 422/67 |
| 2008/0025878 A1 | * | 1/2008 | Schacher | B01L 3/50851 422/400 |
| 2008/0159915 A1 | * | 7/2008 | Yu | G01N 35/08 422/68.1 |
| 2008/0176290 A1 | | 7/2008 | Joseph et al. | |
| 2010/0029000 A1 | * | 2/2010 | Zhong | C12M 23/12 435/383 |
| 2011/0287447 A1 | * | 11/2011 | Norderhaug | B01L 3/0275 435/7.1 |
| 2012/0118954 A1 | * | 5/2012 | Hagen | G01N 35/00732 235/385 |
| 2012/0160091 A1 | * | 6/2012 | Dadd | F16F 1/027 92/132 |
| 2012/0244048 A1 | * | 9/2012 | Teng | B01L 7/04 422/562 |
| 2013/0330818 A1 | * | 12/2013 | Koeda | C12M 41/12 435/303.1 |

\* cited by examiner

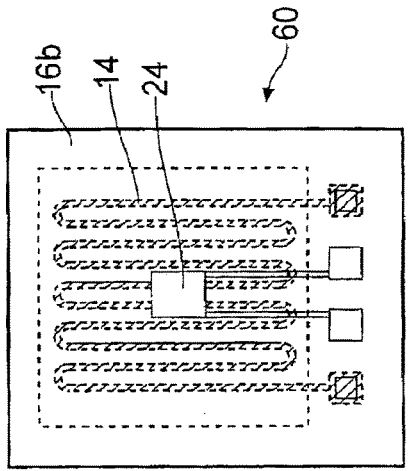
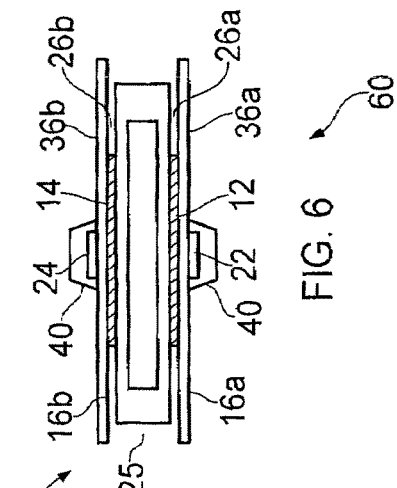
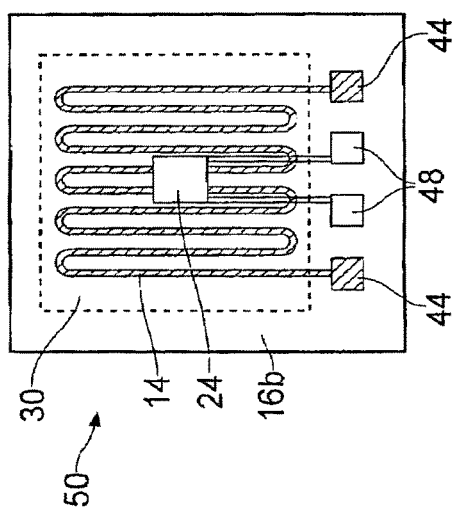
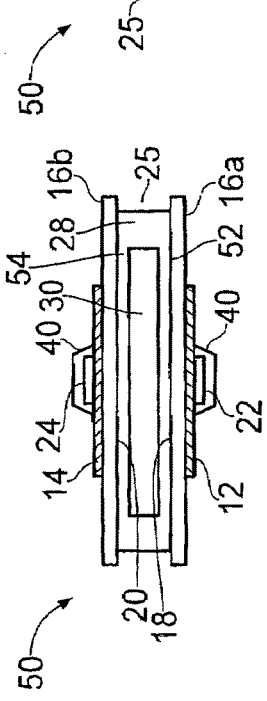
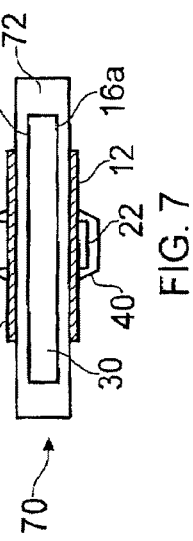

DEVICE AND METHOD FOR HEATING A FLUID CHAMBER

FIELD

The present invention relates to devices, apparatus, systems and methods for heating a fluid chamber, in particular applied to a thermocycler device and method of controlling a thermocycling reaction.

BACKGROUND

Devices for heating a fluid chamber, in which a temperature sensitive or temperature-initiated chemical reaction takes place, typically comprise a heater and a temperature sensor. The heater is controlled thermostatically to maintain a desired temperature so that it can be sensed by the sensor. In some circumstances, a reaction requires the reactant to be exposed to two or more different temperatures sequentially. Predicting the precise amount of heat to be applied, the instant energy is to supplied and the rate of supply of energy (heat) is no always straightforward because a time constant for the response of a system depends on many factors, including the geometry and physical structure of the fluid chamber, the heater and the sensor.

In particular, in polymerase chain reaction (PCR) amplification of DNA, the reaction is cycled between two or more, (typically three), different temperatures and rapid transition between temperatures as well as accurate maintenance of a temperature after a transition, are needed for optimal results. Frequently, as in PCR, a fluid chamber is provided as part of a fluid container removable from a device (termed a thermocycler in the context of PCR) which comprises the heater and temperature sensor.

In such cases the actual temperature in the fluid chamber and the time constant for heating depend on: the nature of the fluid container; and the heat transfer coefficient between the heater and the fluid container. Generally, the actual temperature within the fluid chamber differs from the temperature being sensed by a sensor on the heater device. Additionally it is advantageous to cycle the fluid chamber rapidly, through the required temperatures in order to complete the reaction quickly. The aforementioned factors therefore can lead to the temperature in the fluid chamber failing to track accurately the temperature applied by a heater device.

Various heater devices have been proposed which typically aim to increase the heat transfer coefficient (by reducing the thermal contact resistance) between the heater and the fluid container. One technique uses heater blocks that enclose the fluid container, thus permitting heating and cooling of the container by air flow over the container. Another technique involves placing the container in contact with a first block at a first constant temperature and then placing the container in contact with a second at a second temperature.

PRIOR ART

U.S. Pat. No. 6,633,785 (Kasahara et al) discloses a thermal cycler and DNA amplifier in which a thermal cycler is provided with a number of containers having a shape in conformity with a shape of micro tubes. Nozzles jet coolant to the respective containing members and a blower supplies coolant to the nozzles. Heaters are wound around the containers and thermocouples are placed in contact with the respective containers. By carrying out independent temperature control of respective micro tubes by the control apparatus, accuracy of temperature control of the respective micro tubes is promoted and the processing efficiency is improved.

This device provides multiple independent PCR heaters, within which a PCR tube sits in a thin polymer holder having a single heater coil wound around it and mounted on the external surface of the holder, a single T sensor is provided on the holder, and the holder is cooled by air flow.

U.S. Pat. No. 8,389,288 (Applied Biosystems LLC) discloses a device for carrying out chemical or biological reactions in a reaction vessel receiving element for receiving a microtiter plate with several reaction vessels, wherein the reaction vessel receiving element has several recesses arranged in a regular pattern to receive the respective reaction vessels, a heating device for heating the reaction vessel receiving element, and a cooling device for cooling the reaction vessel receiving element. Individual segments are thermally decoupled from one another, and each segment is assigned a separate heating device which may be actuated independently of the others. By means of the segmentation of the reaction vessel receiving element, it is possible for zones to be set and held at different temperatures.

United States Patent Application US2008/0032347 (Roche Molecular Systems) described a system with a sensor element for monitoring heating and cooling, the system comprising: a cartridge and a device for heating and cooling a mixture in a controlled manner by sensing the temperature of the mixture with at least one sensor element. This system provides one or more PCR fluid chambers in a fluid container that fits to a heat transfer surface on a heater device comprising a single heater positioned below the heat transfer surface. The position at which each chamber of the container contacts the surface has a first temperature sensor in the centre of the heat transfer surface and a second sensor adjacent the area of contact of the chamber.

United States Patent Application US2010/0218600 (Becton Dickinson) describes a device and method for determining the quantity of substance in small cavities. The method simultaneously determines the mass, volume and type of samples in a plurality of small cavities, such as wells in microtiter plates. The rate at which samples heat and cool depends on a number of variables including the mass of the sample. The determination of the substance volumes in the individual cavities is therefore based on temperature measurement. The simultaneous capturing of the sample temperature in the individual cavities can advantageously be performed by an infrared camera functioning as a detector.

This apparatus provides a means for measurement of the volume in a PCR reaction well using a complex optical arrangement that relies on visualisation of the meniscus of the liquid in the well from above, and so is poorly suited for general applications where a fluid container may have a lid and in which the lid may be heated to provide a more uniform thermal environment inside the container.

U.S. Pat. No. 7,049,558 (Arcturas Biosystems) discloses an apparatus and method for heating microfluidic volumes and moving fluids, temperature control, concentration, volume measurement and transportation of microfluidic volumes. The device includes one or more heating elements having a resistive material whose properties vary with temperature. The heating elements are formed into a laminar body that may be located in a variety of geometries and/or easily married to a second body including micro-well plates, micro-centrifuge tubes and microfluidic circuits.

This apparatus discloses heater devices formed on a thin film substrate that is then formed into shape to heat a volume of liquid contained within the shape or in a liquid containing second body of the same shape bonded to it. The heater devices comprise a heater material with a temperature coefficient of resistance contacting two conductive electrodes. One or more heaters are disclosed, and the heating elements form one or more temperature sensors.

United States Patent Application US2012/0309990 (Streck Inc) discloses: a thermocycling device and a method of operating a thermocycler instrument. The instrument includes a sample holder, at least one thermal cycling element, and at least one first and second temperature sensors, for causing the sample holder containing the at least one sample to undergo polymerase chain reaction amplification by repeated cycling between at least a denaturation heating stage and an annealing cooling stage. The first temperature corresponding with the temperature of the sample holder is monitored using the at least one first temperature sensor, and a second temperature corresponding with the temperature external of the sample holder is monitored using the at least one second temperature sensor. Based upon the first temperature and the second temperature, the power that is delivered to the at least one thermal cycling element of the instrument is dynamically controlled.

In general, there is a trade-off between precision of temperature control and speed of transition between two temperatures. However, existing systems rely on a known good quality of thermal communication (i.e. low thermal contact resistance) between the heater and the fluid container.

Prior art devices are known which attempt to measure thermal communication in order to confirm correct operation, but these rely on a temperature sensor on or within the fluid container. This is disadvantageous as it requires a modified fluid container and risks contaminating the liquid.

There is therefore a need for a device that is able to detect and optionally compensate for poor thermal contact. Additionally, in some cases accurate knowledge of the volume of the liquid is needed, for example to quantify the amount of a species, for example DNA copies, in the liquid. This is particularly important if the reaction runs at high temperatures, as in the case of PCR, where evaporation during the course of the reaction is a known source of error. Again existing systems provide examples of measurement of volume of the liquid using optical techniques, but not in a manner that is easy to implement and at a sufficiently low cost that is suitable for use in simple thermocyclers.

Further, existing apparatus and methods do not in general provide for independent control of a number of different reactions having different temperature cycling requirements in either temperature or timing, as they tend to use large, high heat capacity heating blocks to achieve good temperature uniformity and stability. It is desirous to provide such independent control to allow multiple reactions to be run at once, and so as to optimise reaction conditions for a single reaction by running it in a range of different cycling parameters.

It is an object of the invention to overcome these limitations in the prior art to provide a heater device capable of improved control over reactions, in particular reactions requiring thermal cycling.

SUMMARY OF THE INVENTION

According to a first aspect of the invention there is provided a heater device which is adapted to receive at least a first and a second heater for heating a fluid container, the heater device including: one or more substrates, each substrate defines a surface which transfers heat from the at least first and from the second heater to the fluid container, a first temperature sensor is in thermal communication with the first heater; a second temperature sensor is in thermal communication with the second heater; and wherein the first and the second heat transfer surfaces are dimensioned and arranged so that, in use, the fluid container comes into contact with them in order to optimise heat transfer therebetween.

Preferably the first heater is disposed on or in a surface of a substrate in thermal communication with a first heat transfer surface within the receiving location; and the second heater is disposed on or in a surface of a substrate in thermal communication with a second heat transfer surface within the receiving location spaced apart from the first heat transfer surface. An advantage with this arrangement is that the first and second heated heat transfer surfaces can be applied simultaneously or sequentially and heating and cooling is achieved rapidly.

Sensors and monitoring equipment may be arranged to take account of the rate of change of a temperature throughout a predefined interval at a particular location and/or the total amount of energy delivered to that location, so as to provide derivate data relating to the speed of heating and/or cooling.

Optionally the at least first and second heaters are detachable and removable from the heater device so that it may be cleaned or repaired or recalibrated or replaced.

Preferably the heater device comprises three heaters each heating a block or portion of a block that is adapted to contact a side or wall of a fluid container. There are three temperature sensors that are provided. One temperature sensor is inside the fluid chamber; one is in contact with or embedded in a block heated by one of the heaters; and the third temperature sensor is inside the chamber is used to check the internal temperature of the chamber against the temperature measured by the sensor on the block.

According to a second aspect of the invention there is provided a heater device to heat a fluid chamber comprising: a first and a second heater each disposed on a substrate and each having a heat transfer surface configured to provide thermal communication with a common fluid chamber; a first temperature sensor proximal to the first heater; a second temperature sensor proximal to the second heater, wherein the second heater and second temperature sensor are spaced apart from the first, the first heater being configured to heat a first region of the fluid chamber and the second heater being configured to heat a second region of the fluid chamber.

In some embodiments the invention provides a heater device to heat a fluid container separable from the heater device comprising: one or more substrates each forming a surface of a receiving location for the fluid container, a first heater disposed on a surface of a substrate in thermal communication with a first heat transfer surface within the receiving location; a second heater disposed on a surface of a substrate in thermal communication with a second heat transfer surface within the receiving location spaced apart from the first heat transfer surface; a first temperature sensor in thermal communication with the first heater; and a second temperature sensor in use is in thermal communication with the second heater, wherein the receiving location is configured to conform to the fluid container such that the first and the second heat transfer surfaces come into contact with the fluid container.

In some embodiments a heater device has a temperature coefficient of resistance and the temperature sensor comprises the heater, temperature being sensed by measuring the resistance of the heater.

Detection of rate of heating may be transverse to the axis of a tube or it may be performed lengthwise along a tube. Depending upon the amount of liquid and the dimensions of a tube, there may be more or less liquid in one orientation and therefore more or less thermal delays in a preferred orientation.

Once a volume of liquid is known it is possible to detect temperature transients in order to determine volume of liquid in a tube or container.

In some embodiments the thermal conduction pathway from the first heater to the first temperature sensor has a greater thermal conductance than that from the first heater to the second sensor and the thermal conduction pathway from the second heater to the second temperature sensor has a greater thermal conductance than that from the second heater to the first sensor.

Advantageously the first temperature sensor is provided on a surface of the substrate closer to the first heater than to the second heater and the second temperature sensor is provided on a surface of the substrate closer to the second heater than to the first heater.

Ideally the device further comprises a control means adapted to control the first heater using data from the first temperature sensor and to control the second heater using data from the second temperature sensor, each heater being controlled independently of the other.

In some embodiments the device comprises a control means adapted to control both the first and the second heaters using data from the first temperature sensor, and in some embodiments to record data from the second temperature sensor. In this way the second temperature sensor acts as a backup measurement source to compare with the first sensor.

The control means may have: a first mode of operation in which it controls both heaters to heat the fluid chamber simultaneously, and a second mode in which it controls the first heater to heat the fluid chamber and measures the temperature of the second sensor against time.

In another embodiment the control means may control the first heater to maintain a first temperature at the first sensor and then to change to maintain a second temperature at the first sensor while measuring the temperature of the second sensor against time.

In some embodiments in the second mode the control means additionally controls the second heater to operate at a constant power while measuring the temperature of the second sensor against time.

In some embodiments the first and second heaters are provided on a common substrate.

A fluid chamber is an enclosed volume adapted to contain a fluid and having one or more walls through which heat may be transferred, and may be for example: a reaction vessel, a tubular vessel such as a PCR (Polymerase Chain Reaction) tube, a tubular chamber such as a capillary, a channel or other volume within a microfluidic device or a flow through reactor.

A fluid container comprises a fluid chamber and its surrounding walls and a closure, which may be permanently part of the heater device or may be adapted to be placed in thermal communication with the heater device and to be removable from it. A fluid container may be in the form of a vessel, a tube, a microfluidic device or a bio- or chemical reaction device or container.

A substrate is a body supporting other components or features of the heater device and may in some embodiments have a sheet form, or be a solid body configured to provide the said features or components, such as a recess within which a fluid container may be received.

Thermal contact between a first entity and a second entity such that heat may be transferred between them.

A first feature being in thermal communication with a second means that a first feature may exchange heat with a second.

An example of a heater is an electrical heater comprising a resistive material, for example a resistive track or a region of resistive material overlying two conducting tracks, and comprises contacts which may be of the same material as the heater or a different material.

An example of a heat transfer surface is a surface heated by a heater adapted to transfer heat to or from an adjoining surface. For example the heater devices of the invention comprise a heat transfer surface heated by each heater. A fluid container that may be removed from the heater device comprises at least one heat transfer surface adapted to contact those on the heater device.

An example of a temperature sensor is a sensor providing an electrical response to temperature, such as a thermistor or a thermocouple. In some embodiments the heater has a temperature coefficient of resistivity and is used as a temperature sensor. A temperature sensor may comprise a temperature responsive element and an electronic interface adapted to provide temperature information to a control means. The interface is ideally associated either with the temperature sensor or forms part of a control means. Data may be transferred from the temperature sensor to the control means in analogue or digital form.

An example of a control means is a computer controlled electronic system that interprets instructions in the form of data, receives data from one or more sensors (such as temperature sensors) and provides an output to control one or more devices, such as heaters, forming part of the device and optionally other components of an apparatus comprising the device, for example, gas flow controllers such as fans and flow diverters, gas flow heaters or coolers, and ancillary components such as barcode or RFID readers. The control means may comprise a computer such as a microprocessor, a data storage means readable by the computer and a user interface or a dedicated electronically programmable device such as a field programmable gate array (FPGA).

The control means may optionally further comprise: communication means to communicate data to or from a display or a further electronic system or data store. The control means may be configured to receive data entered by a user, received from a remote electronic system or data source, read from a data storage means associated with a fluid container such as a barcode or RFID device, and to control operation of the heater device or apparatus in response to such data. The control means may be configured to output data to a display, a printer, a remote electronic system, computer or data storage means, such as a data storage means associated with a fluid container.

Means may be provided in order to detect the presence of a PCR tube and/or to detect the volume of liquid within the PCR tube and optionally to configure the means to provide a signal representative of the presence or contents of the PCR tube.

The control means may control the heaters or other devices and powering them directly and controlling the power dissipated in them, or may send control data to a separate heater power supply connected to the heater contacts. The control means may measure and record the power supplied to each heater.

In some embodiments the one or more substrates form part of the wall of the fluid chamber. In this way the heater device may be permanently bonded to or may form part of the fluid chamber.

In some embodiments the device comprises a separable fluid container comprising the fluid chamber and removable from and replaceable into the heating device, mounted in thermal communication with the heat transfer surfaces.

In this way the heater device comprises a first and a second heater in thermal communication with a fluid chamber in use, each heater having a temperature sensor in thermal communication with it. The thermal conduction pathway from first heater to the first temperature sensor has a greater thermal conductance than that to the second sensor and the thermal conduction pathway from the second heater to the second temperature sensor has a greater thermal conductance than that to the first sensor. Therefore the first temperature sensor is usable to control the first heater and the second temperature sensor to control the second heater independently of the first.

In some embodiments in a first operating mode the control means controls both heaters to heat the fluid chamber simultaneously. The first and second heater may be set to the same control temperature Tc by the control means, the power dissipation in each heater being controlled in a feedback loop using data from the proximal temperature sensor. Minor differences in heat loss from the first and the second heater may in this way be compensated individually, allowing an improved uniformity of heating of the fluid chamber.

In some embodiments the heater device comprises a plurality of heaters configured to heat a common fluid chamber, each having a temperature sensor in thermal communication with the heater and a control means configured to control each heater using data from the temperature sensor.

In typical operating circumstances, when the heaters are first turned on, or stepped to a higher or lower temperature, subsequently kept constant under feedback control, the temperature Tr at a point inside the fluid chamber will take an amount of time to reach the new temperature.

The time constant for change in the temperature Tr inside the fluid chamber will depend on factors including: the chosen position at which Tr is estimated the position may be at the mid-point of the fluid chamber, such as at the centroid of the fluid chamber, the centroid of an expected liquid volume within the fluid chamber, a position on the axis of the chamber, or a position at or near the wall of the fluid chamber; the geometry of the fluid container and the fluid chamber within it, including the thickness of the wall of the fluid container; the material of the fluid container, its thermal conductivity and specific heat capacity; the volume of the liquid and its disposition within the fluid chamber; the heat transfer coefficient between the heat transfer surfaces and the outer wall of the fluid container; cooling of the outer surfaces of the fluid container not in contact with the heaters, primarily by convection; heat transfer within the fluid chamber by convection within the liquid, between regions heated by the heat transfer surfaces and regions of the wall cooled by convection.

The invention provides a device and a method for use in particular in thermocycling reactions such as PCR, to derive Tr in order to ensure that Tr has reached within a chosen range of a control temperature Tc, and that Tr stays within a range of Tc for a chosen minimum length of time following a temperature transition during each temperature cycle. Also provided is a device and method for deriving the time tmin following a change in temperature of the heaters after which Tr has reached within a chosen range of Tc, such that in a thermocycling reaction the cycle time is long enough for substantially all the liquid to have reached within that range of Tc.

According to the invention, when the parameters of the heater device, the fluid container and the liquid, and also the liquid volume are known, it is possible to model tmin and Tr (time) and to use the results to control the heater device. In some embodiments certain parameters are unknown, or subject to error, and the heater device and method of the invention provide means to test for one or more of these parameters.

Additionally, the estimated values of tmin and Tr (time) depend on the heat transfer coefficient hc between the heaters and the outer wall of the fluid container. In some embodiments the heater device and method of the invention provides means to estimate hc and hence to optimise the estimates of tmin and Tr (time).

Accordingly, in a second operating mode the control means applies power to the first heater while recording the temperature at the second temperature sensor as a function of time, referred to as T2(time) data. This allows the control means to derive information about the thermal conduction pathway between the first heater and the second temperature sensor, and to derive parameters including:

The liquid volume;
The fluid container data;
The heat transfer coefficient hc;
Whether the one or more T2(time) values are outside an expected range of values, for example outside the range of model T2(time) values stored in the data store or found from an algorithm.

This provides an indication that the heat transfer resistance between the heat transfer surfaces and the fluid container is above a control value (i.e. hc is below a control value), implying that a fluid container comprising the fluid chamber is either not present, does not match an expected fluid container for which data is present in the data store, or is in poor thermal communication with the heat transfer surfaces, for example be being incorrectly located at the receiving location.

In some embodiments the T2(time) data is used together with liquid data, liquid volume and fluid container data in an algorithm to derive the heat transfer coefficient hc. In some embodiments the derived value of hc is used in a process to derive tmin or Tr(time) as described herein.

In this way the control means is adapted to estimate values of Tr and tmin as described above, and in some embodiments is adapted to estimate the volume of liquid within the fluid chamber and to alert a user if the volume differs from a pre-determined control volume or acceptable range of volumes. In some embodiments the control means is adapted to alert a user if the fluid container is missing or is incorrectly positioned against the heat transfer surfaces.

In some embodiments the control means is adapted to control the power supplied to a heater in order to maintain a constant temperature at the heater. In some embodiments the control means is adapted to measure the power supplied to a heater at one or more constant temperatures, and/or to record the power as a function of time to measure how the power needed to maintain a constant temperature changes with time. In this way the control means may be adapted to measure the loss of heat from the heater device, the fluid container, or both to convection at a given temperature, and may be adapted to measure the heat flow into the liquid following a change in temperature of the heater.

In some embodiments in which a reaction to be carried out in the fluid chamber has an initiation temperature Ti at which the reaction starts, the control means is configured such that when in the second mode of operation, for example to operate a calibration process, the heaters are kept to a temperature below the initiation temperature. In this way the control means and a method of the invention are adapted to derive values as described herein without affecting the time of initiation or the time course of the reaction. For example, the control means may control the first heater such that the temperature T1 at the first temperature sensor is less than the initiation temperature by up to 10° C., more than 10° C., more than 20° C., or more than 30° C.; in a PCR protocol which initiates at a temperature of 95° C. the control means may control the first heater such that the temperature T1 at the first temperature sensor is below 95° C., such as below 80° C., below 70° C., or below 60° C.

Embodiments of the invention will be described below in which the above principles are applied.

The heater device may have a range of configurations, in each of which the first temperature sensor is in closer thermal communication with the first heater than with the second heater and the second temperature sensor is in closer thermal communication with the second heater than with the first heater. Accordingly, in some embodiments the heater device comprises one of more of the following configurations:

A temperature sensor is provided proximal to a heater on a common substrate, the heater device comprises two or more substrates;

The first and second heaters are both provided on a first surface of a common substrate and the first and second temperature sensors are also mounted on the first surface, proximal to the heaters;

Each heater comprises an extended resistive heater track occupying a heated area of a substrate having a perimeter substantially defined by the outer dimensions of the heater track, the first sensor being located within the first heated area and the second sensor is located within the second heated area, wherein the first and second heated areas are adjacent and do not overlap;

In some embodiments the temperature sensor is mounted on the first surface of the substrate and the heater track is disposed on the first surface proximal to and wholly or substantially surrounding the temperature sensor;

A heater is provided on a first surface of a substrate and the temperature sensor is mounted on top of the heater;

A heater is provided on the first surface of the substrate and a temperature sensor is provided on the second surface, wherein the first surface is the heat transfer surface;

The substrate comprises a planar sheet, the heater is provided on the first major surface and the heat transfer surface is the second major surface opposing the first surface;

The device comprises a first thermally conducting layer in thermal communication with the substrate and the first temperature sensor and a second thermally conducting layer in thermal communication with the substrate and the second temperature sensor;

The device comprises an insulating layer substantially or wholly covering the first and second temperature sensors.

In some embodiments the heat transfer surfaces are shaped to contact a fluid container separable from the heater device in use. Accordingly in some embodiments the heater device comprises some of all of the following features:

The heaters are provided on a substrate formed to provide a shaped heat transfer surface.

The first and second heaters are disposed within a recess adapted to receive the fluid container, the first and second heat transfer surfaces being provided within the recess The recess has a substantially conical region to receive a fluid container having a conical portion of its external profile, such as a PCR reaction tube.

The recess has a substantially circular horizontal cross section and the second heater is provided at a location diametrically opposed from the first heater.

The substrate comprises a planar sheet form, shaped to form the recess, the first surface of the substrate forming the heat transfer surface on the inside of the recess.

A first and a second heater are provided on the first surface.

A temperature sensor is provided in thermal communication with the heater on the first surface.

A temperature sensor is provided on the second surface of the substrate in thermal communication with the heater within the perimeter of the heated area of the heater.

A heater is provided on the second surface of the substrate within the area of the sides of the recess.

A heater device according to the invention, comprising a substrate formed from a thin polymer sheet shaped to form a heat transfer surface, provides the advantage that it has a low heat capacity so its temperature responds rapidly to a change in power input to the heaters. Additionally, the device will respond rapidly to cooling by convection heat loss and, being thin, allows ready heat conduction through the substrate in cooling a reaction chamber in thermal communication with it.

In some embodiments the control means comprises a computer, a data store and a control program, wherein the control means is configured to: receive fluid container data, liquid data and the liquid volume and/or control both the first and the second heaters at a known temperature to heat the fluid container and/or use fluid container data, liquid data and liquid volume to derive a temperature Tr within the fluid chamber; and or use the value of Tr to control the first and the second heaters.

In some embodiments the control means is adapted to receive fluid container identification data from a remote data source, and to use this to identify fluid container data stored in the data store. The fluid container identification data may comprise for example a part number, bar code, choice of fluid container made by a user via a user interface. In some embodiments the remote data source may comprise a data source associated with the fluid container such as a bar code or RFID chip, or may comprise a user interface, a computer or a data store remote from the heater device. In some embodiments the device comprises one or more of: a barcode reader, an RFID reader, a user interface comprising a display and data input means.

In some embodiments the control program comprises a lookup table in the data store comprising temperature relationship data relating Tr to a value of T1 or T2 for parameters of the fluid container data, liquid data and liquid volume. Such temperature relationship data may be used to drive Tr from T1 and/or T2.

In this way the control means may know the type of fluid container, for example a PCR tube, in use and may use temperature relationship data specific to that fluid container, stored in the data store as part of a calibration process.

In some embodiments the control program comprises an algorithm to derive temperature relationship data using fluid container data, liquid data and liquid volume as parameters.

In some embodiments the control program comprises an algorithm to derive a minimum heating time tmin following a change of heater power of the first or the second heater after which a temperature Tr within the fluid chamber is within a chosen range of one of T1 and T2. According to the embodiment the chosen range may be within ±10° C., ±5° C., ±2° C. or ±1° C. of T1 or T2.

In some embodiments the control program comprises a lookup table in the data store relating tmin to the fluid container data and liquid data. In some embodiments the control program comprises an algorithm relating tmin to the fluid container data and liquid data.

In some embodiments the control means is configured to indicate the value of tmin to a user and/or control one or both of the first and the second heaters such that they are powered for a minimum of time tmin in any one period of heating.

In some embodiments the control means is adapted to measure and record the power as a function of time, P(time) needed at one or both of the first and second heaters to maintain a constant temperature following a change, such as a step change, in T1 and/or T2 to form P(time) data, then to derive from P(time) data the degree to which Tr has approached T1 or T2. As Tr approaches the external temperature, P(time) will tend to a constant value. The control means is adapted in these embodiments to derive the approach to a constant value of Tr from the approach to a constant value of P(time), for example the control means may comprise an algorithm to relate Tr(time) to P(time).

In some embodiments the control means is configured to control the first and the second heaters to maintain Tr within a chosen range of a control temperature Tc. In this way one or both of the first and the second heaters may be controlled at a temperature T1, T2 above Tc in order to increase the rate of heat transfer from the heat transfer surface to the fluid chamber. Tr may in this embodiment be an estimate of temperature within the liquid near the wall of the fluid chamber. As the estimated value of Tr(time) rises with time after the temperature step, T1 and T2 may be lowered so that Tr at the fluid chamber wall does not exceed the upper range around Tc. In this way the heaters may be overdriven to speed the rate of change of temperature and equilibration within the fluid chamber.

It will be understood that in certain embodiments the control means may be configured to control the second heater to heat the fluid chamber while measuring the temperature T1 at the first temperature sensor to provide T1(time) data that may be used analogously to the T2(time) data in processes as described herein.

In some embodiments the device is adapted to carry out a thermocycling reaction within the fluid chamber, the control means being configured to:
Derive a minimum heating time tmin as described herein,
Control one or both of the first and the second heaters to heat the fluid chamber until one or both of T1 and T2 reach a first chosen control value Tc1,
Control one or both of the first and the second heaters to maintain one or both of T1 or T2 within a chosen range of Tc1 for a time t1,
Control one or both of the first and the second heaters to heat the fluid chamber until one or both of T1 and T2 reach a second chosen control value Tc2,
Control one or both of the first and the second heaters to maintain one or both of T1 or T2 within a chosen range of Tc2 for a time t2,
Wherein t1 and t2 are both greater than or equal to the minimum heating time tmin.

In some embodiments the a computer operates in accordance with instructions from a control program comprising an algorithm to carry out the above steps.

In some embodiments the device is adapted to carry out a thermocycling reaction within the fluid chamber, the control means being configured to:
Derive temperature relationship data relating Tr to one or both of T1 and T2,
Control one or both of the first and the second heaters to heat the fluid chamber while receiving data from the first and the second temperature sensors, and use the temperature relationship data together with values of T1 and/or T2 to:
Derive a value of Tr,
Control the first and the second heaters to maintain Tr within a chosen range of a first control temperature Tc1 for a first time t1, and
Control the first and the second heaters to maintain Tr within a chosen range of a second control temperature Tc2 for a second time t2.

In some embodiments the device is adapted to control the first and the second heaters to maintain Tr within a chosen range of a third control temperature Tc3 for a third time t3. In some embodiments the control means is programmable by a user to provide a plurality of cycles of actions as above.

According to the embodiment the chosen range for the heater device referred to above may be within ±10° C., ±5° C., ±2° C. or within ±1° C. or within a range of less than ±1° C. of a control temperature.

According to the embodiment Tr may be chosen to lie on an axis of symmetry of the fluid chamber, for example at a centre of symmetry of the fluid chamber, for example at the centroid of the fluid chamber. In some embodiments for example as described above the control means may be configured to estimate Tr at a location close to the wall of the fluid chamber, or at a plurality of locations within the fluid chamber.

In some embodiments in particular adapted for use in thermocycling reactions such as PCR, the device and method are adapted to determine the liquid volume in a fluid chamber, for example to do one or more of:
(i) to check that the initial filled volume is correct, such as within a first range of a control volume;
(ii) to check that the final volume after the reaction is within a second range of the control volume, so checking that evaporation during the reaction is less than a chosen limit;
(iii) to measure the amount of evaporation during the reaction and to use the measured loss of volume to correct a measurement of an analyte in the liquid, for example the concentration of a PCR product.

Accordingly, in some embodiments the control means is configured to:
(i) Control the first heater to maintain a first constant temperature T1,
(ii) Control the first heater to change T1 from the first temperature to a second constant temperature,
(iii) Read data from the second temperature sensor as a function of time and store it in the data store to form T2(time) data, and
(iv) Use fluid container data and liquid data stored in the data store as parameters in an algorithm to derive the liquid volume from T2(time) data.

In some embodiments the control means is configured to record the power supplied to one or both heaters in order to maintain a constant temperature at that heater to form P(time) data. In some embodiments the control means is configured to supply power to the second heater while the first heater is maintained at a constant temperature T1.

In some embodiments the control program is configured to compare the liquid volume with a control volume stored in the data store and indicate to a user a fault condition if the liquid volume differs from the control volume.

In this way the control means is able to indicate if a fluid chamber contains a liquid volume outside an acceptable range. According to the embodiment the chosen range may be within ±20%, ±10%, ±5%, ±2% or less than ±2% of the control volume.

In embodiments in which a separable fluid container is used is it of value to check that it is properly located on the heat transfer surfaces before the reaction process starts. Therefore in some embodiments the control means is configured to use T2(time) data to derive a value characteristic of the heat transfer coefficient between one or more heat transfer surfaces and the fluid container and to indicate to a user a fault condition that the heat transfer coefficient is greater than a control value.

Accordingly in some embodiments the control program comprises an algorithm adapted to:
(i) Control the first heater at a temperature T1 and receive T2(time) data from the second temperature sensor and store it in the data store,
(ii) Compare the T2(time) data with model T2(time) data stored in the data store associated with parameters of fluid container data liquid data and liquid volume for the fluid container and liquid being used, and
(iii) Determine whether T2(time) data is within a chosen range of the model T2(time) data.

In this way the control means is able to indicate if in the case of a separable fluid container, the container is absent, or not in good thermal contact with the heater device, such as in the case of a fluid container that has been inserted incorrectly by a user into a heater device.

In some operational situations the fluid container in use may not be a recognised type and so fluid container data may not be present initially in the data store. Therefore in some embodiments the control means is configured to derive fluid container data and/or liquid data using measurements of T2(time) made when an empty fluid container is in thermal contact with the device and heated by the first heater.

Accordingly in some embodiments the control program comprises an algorithm configured to:
(i) Heat an empty fluid container by applying a temperature change to the first heater while reading T2(time) data,
(ii) Store T2(time) data in the data store to form calibration temperature relationship data,
(iii) Use the calibration temperature relationship data to derive fluid container data.
(iv) Store the fluid container data in the data store for use as a parameter in another algorithm as described herein.

In these embodiments the algorithm may relate the heat flow characteristics of the empty fluid container to those when liquid is present. In particular, the algorithm may relate conduction around the circumference of the fluid container between the first heater and the second sensor when the fluid chamber is empty to conduction radially through the wall of the fluid container when the liquid is present.

In thermocycling diagnostic reactions such as for PCR there is a requirement to run multiple reactions in parallel. Accordingly in some embodiments the invention provides an apparatus comprising a plurality of heating devices as described herein and a control means configured to control the heating devices independently.

In some embodiments the control means is configured to carry out some or all of the processes described herein for each heating device independently or for groups of the heating devices jointly.

In some embodiments the apparatus comprises a gas flow means to direct gas over the surface of a heater device and over a fluid container when in position in the heater device. In some embodiments the gas flow means comprises a fan and the gas is air. In some embodiments the gas flow means comprises a source of compressed gas.

In some embodiments the apparatus comprises gas flow cooling means to cool the gas before it is directed over the heater device and fluid container. Such cooling means may comprise one or more of a heat exchanger, a Peltier device, a refrigeration means comprising a liquid coolant, and expansion of a compressed gas through an orifice.

The gas flow is directed over the heater device to control the rate of convection heat dissipation from the heater device and the fluid container. In some embodiments this gives improved control over the rate of convection heat loss, which without the forced gas flow would depend on natural convection and so would tend to be subject to greater variation, in particular depending on the temperature of the heater device and fluid container. In some embodiments in which the apparatus is a thermocycler, for example for a PCR reaction, there is a need for rapid cooling of the heater device and the fluid container, so forced gas convection allows for a large degree of convection heat loss.

In some embodiments the control means is configured to control the gas flow rate, for example by controlling the speed of a fan driving the gas flow or by controlling a valve to control the rate of flow of gas from a gas source, and/or to control a gas cooling means.

In some embodiments the apparatus comprises:
(i) A housing having a lid to define an interior space,
(ii) A plurality of separate heater devices as described herein located within the housing and thermally isolated from each other, each being configured to receive a separate removable fluid container,
(iii) A control means configured to control each heater device independently,
(iv) A gas flow means within the housing to cause gas flow over the heater devices, In some embodiments the heater devices comprise a recess to receive the fluid containers.

In some embodiments the fluid containers are reaction tubes, such as PCR tubes.

In some embodiments the apparatus comprises a user interface comprising data input means, data output means, a display means.

In some embodiments the apparatus comprises a control program adapted to carry out one or more of:
A calibration process as described herein using one or more empty fluid containers,
A calibration process as described herein using one or more fluid containers containing a known liquid volume,
A reaction process as described herein using a liquid in one or more fluid containers, and
Report to a user interface reaction data related to the fluid container in each heater device.

In some embodiments the reaction data comprises one or more of: a temperature of the heater device; a control temperature set by the control means for a heater device; confirmation of the presence of a fluid container in thermal contact with a heater device; the presence of a fluid container that differs from a fluid container that has been designated for use; an estimated volume of liquid within the fluid container; confirmation that the liquid volume is within a chosen range of a control volume; the change in the estimated volume of liquid before and after a process of heating the fluid container.

In some embodiments the apparatus is a thermocycling device configured to run a plurality of independent thermocycling reactions in parallel.

In some embodiments the apparatus is configured to measure a quantity of or within the liquid, for example from the list of: liquid volume, absorbance, fluorescence, turbidity, optical activity (polarisation), conductivity, temperature, pH.

In some embodiments the apparatus is configured to measure the liquid volume at a first time point during a reaction process, for example before the process begins, and at a second time point, for example after the process ends. In some embodiments the apparatus is configured to measure a quantity and to use the measurement of the volume to change a reported value of the quantity. In some embodiments the first quantity may comprise in a PCR reaction a copy number or concentration derived from an optical method.

In this way the apparatus is configured to correct a measured quantity for evaporation, in which the evaporated volume is found from an estimate of the liquid volume before and after the reaction.

According to a second aspect the invention provides a method for heating a fluid chamber using a heater device as described herein.

A method for heating a fluid chamber using a heater device as described herein comprises the steps of:
(i) Heating the fluid container using both the first and the second heaters,
(ii) Receiving data from the first temperature sensor and using the data to control the first heater,
(iii) Receiving data from the second temperature sensor and using the data to control the second heater.

In some embodiments the method comprises the steps of:
(iv) Using fluid container data and liquid data to derive a temperature Tr within the fluid chamber,
(v) Using the value of Tr to control the first and the second heaters.

In some embodiments the method comprises the additional step of inputting to the data store fluid container data, liquid data and liquid volume.

In some embodiments the invention provides a method of using a heater device comprising a control means and a data store comprising a lookup table for heating a fluid chamber, comprising the further steps of:
(i) Using fluid container data liquid data and liquid volume to identify temperature relationship data within the lookup table.
(ii) Using temperature relationship data to control the first and the second heaters.

In some embodiments the method includes the further step of providing temperature relationship data within the lookup table comprising the steps of: heating using both the first and the second heaters a selected fluid chamber containing a known liquid volume and having a temperature sensor at a point within the liquid and storing Tr(time) data from the sensor in the lookup table together with values of T1 and/or T2 to form the temperature relationship data.

In some embodiments the method comprises the step of deriving a minimum heating time tmin following a change of heater power of the first or the second heater after which a temperature Tr within the fluid chamber is within a chosen range of one of T1 and T2. The minimum heating time tmin may be derived for example from a lookup table of values of Tr versus time associated with fluid container data, liquid data and liquid volume for the fluid container and liquid being used.

In some embodiments the method comprises the step of controlling one or both of the first and the second heaters to maintain Tr within a chosen range of a control temperature Tc. According to the embodiment the chosen range may be within ±10° C., ±5° C., ±2° C., ±1° C. or less than ±1° C. of Tc.

In some embodiments the invention provides a method for controlling a thermocycler comprising the steps of: controlling the first and the second heaters to maintain Tr within a chosen range of a first control temperature Tc1 for a first time t1, and controlling the first and the second heaters to maintain Tr within a chosen range of a second control temperature Tc2 for a second time t2.

Ideally the aforementioned steps are then repeated as part of a plurality of cycles of steps in the method.

In some embodiments the method comprises the step of controlling the first and the second heaters to maintain Tr within a chosen range of a third control temperature Tc3 for a third time t3.

In some embodiments the invention provides a method to carry out a thermocycling reaction within the fluid chamber, comprising the steps of:
(i) Deriving a minimum heating time tmin as described herein,
(ii) Controlling the first and the second heaters to heat the fluid chamber until one or both of T1 and T2 reach a first chosen control value Tc1,
(iii) Controlling the first and the second heaters to maintain one or both of T1 or T2 within a chosen range of Tc1 for a time t1,
(iv) Controlling the first and the second heaters to heat the fluid chamber until one or both of T1 and T2 reach a second chosen control value Tc2,
(v) Controlling the first and the second heaters to maintain one or both of T1 or T2 within a chosen range of Tc2 for a time t2,
Wherein t1 and t2 are both greater than or equal to the minimum heating time tmin.

In some embodiments times t1 and t2 may be entered by a user.

In some embodiments times t1 and t2 may be set by a data file describing an experimental protocol stored in the data store.

In some embodiments the method comprises the step of alerting a user if an entered value of one of t1 and t2 is less than tmin.

In some embodiments the method comprises the step of setting one of t1 and t2 such that they are greater than or equal to tmin.

In some embodiments the method comprises the step of mounting a separable fluid container containing a reaction mixture in thermal contact with the heating device.

In some embodiments the method comprises the further steps of storing fluid container data in the data store and receiving fluid container identification data and using it to select fluid container data for use in the method.

In some embodiments fluid container identification data may be received from a user interface by being entered by a user and/or may be read by a reader connected to the control means from an identification means associated with the fluid container, such as a bar code, a number code, an RFID chip, provided on the fluid container or on packaging associated with it.

In some embodiments the liquid data may be received from a user interface as above.

In some embodiments of the method the type of fluid container is a preferred type and data on it is held in the data store while the liquid volume is unknown or is to be measured. Accordingly, in some embodiments the method comprises deriving the volume of liquid in the fluid chamber comprising the steps of:
(i) Controlling the first heater to maintain a first constant temperature T1
(ii) Controlling the first heater to change to a second constant temperature T1
(iii) Reading T2(time) data and storing it in the data store,
(iv) Using the T2(time) data and stored fluid container data in the data store in an algorithm to derive the liquid volume.

In some embodiments the method comprises the further step of
Using the derived liquid volume in an algorithm to control one or both of the first and the second heaters.

In some embodiments the method comprises the steps of:
(i) Providing one or more model T2(time) data sets in the data store, the model T2(time) data sets each having as a parameter a value of the liquid volume
(ii) Receiving fluid container identification data,
(iii) Using fluid container identification data to select one or more model T2(time) data sets in the data store,
(iv) Comparing T2(time) data with the one or more model T2(time) data sets to determine the set having the best match, and identifying the liquid volume parameter for that data set as the liquid volume.

In some embodiments of the method the type of fluid container is not a preferred type and no data is held on it in the data store, and the liquid volume is provided by the user.

In some embodiments the method provides a calibration process to derive fluid container data comprising the steps of:
(i) Receiving liquid data and the liquid volume,
(ii) Providing an empty fluid container in thermal communication with the heater device,
(iii) Controlling the first heater to maintain a first constant temperature T1
(iv) Controlling the first heater to change to a second constant temperature T1 while measuring T2(time) data,
(v) Storing the T2(time) data in the data store to form calibration temperature relationship data,
(vi) Using liquid data and calibration temperature relationship data to derive temperature relationship data characteristic of the liquid volume,
(vii) Storing temperature relationship data in the data store.

In some embodiments the method controls the heaters using the derived fluid container data, the method comprising the additional steps of:
(viii) Providing a fluid container containing the said liquid volume of liquid in thermal communication with the heater device,
(ix) Using the said Tr(time) data to control one or both of the first and the second heaters to heat the liquid.

In some embodiments the temperature relationship data is derived by comparing the calibration temperature relationship data with data stored in a lookup table in the data store.

In some embodiments the temperature relationship data is derived using an algorithm stored in the data store.

In some embodiments the invention provides a method for estimating the volume of a liquid within a heated fluid chamber using a heater device and a method as described herein.

In some embodiments a method for estimating the volume of a liquid in fluid containers in a thermocycler comprising one or more heating devices as described herein comprises the steps of:
(i) Receiving data comprising the first liquid volume at a first time point,
(ii) Optionally reporting to a user interface one or both of the first value of the liquid volume and that the liquid volume is outside a chosen range of a control volume,
(iii) Heating one or both of the first and the second heaters to carry out a reaction in the fluid chamber,
(iv) Deriving a second liquid volume at a second time point,
(v) Finding the loss in volume between the first and the second time points, In some embodiments the first liquid volume is received from a process of deriving the volume as described herein. In some embodiments the first liquid volume is received from a user interface, for example input by a user, or from another data source.

In some embodiments the method comprises the step of reporting one or both of the lost volume and the condition that the lost volume is outside a range of a control value. According to the embodiment the chosen range may be within ±20%, ±10%, ±5%, ±2% or less than ±2% of the first volume.

In some embodiments the method comprises the step of correcting a data value derived from a measurement during the thermocycling process using the value of the lost volume.

In some embodiments the method is carried out in an apparatus comprising a plurality of heater devices and fluid containers and comprises one or both of the steps of deriving and reporting to a user interface the liquid volume within each fluid container and whether the derived volume of liquid within each container is within a chosen range of a control volume.

Preferred features of the second aspect of the invention are as for the first aspect mutatis mutandis

BRIEF DESCRIPTION OF THE FIGURES

FIG. 3 shows a top view of a further embodiment of a heater device having a fluid container in thermal contact with it;

FIG. 4 shows a cross section of the embodiment shown in FIG. 3;

FIG. 5 shows a top view of a further embodiment of a heater device according to the invention having a fluid container in thermal contact with it;

FIG. 6 shows a cross section of the embodiment shown in FIG. 5;

FIG. 7 shows a cross section of a further embodiment of a heater device according to the invention;

DESCRIPTION OF EMBODIMENTS

For the avoidance of doubt, a temperature read by the first temperature sensor will be referred to as T1 and a temperature read by the second temperature sensor as T2.

Figure 1:
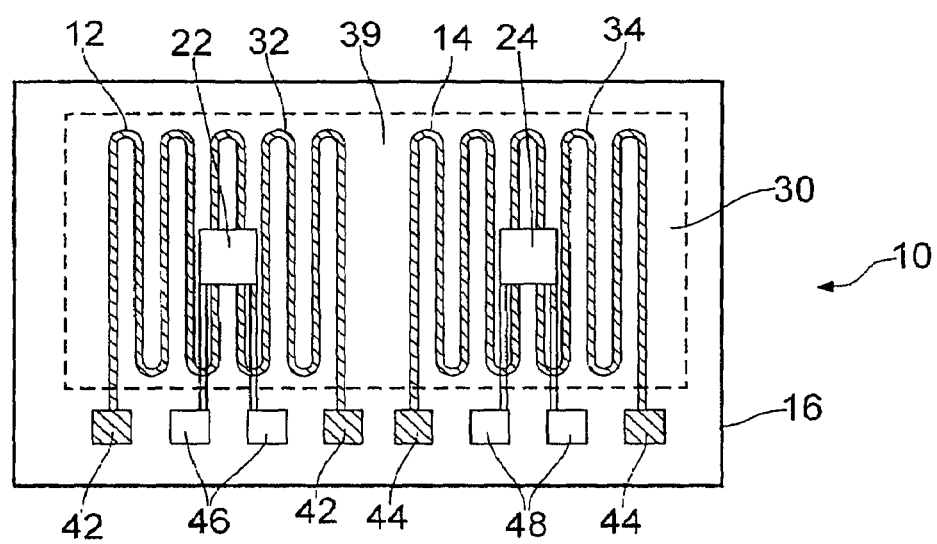
FIG. 1 shows a top view of an embodiment of a heater device according to the invention and a fluid container in thermal contact with it.
Figure 2:
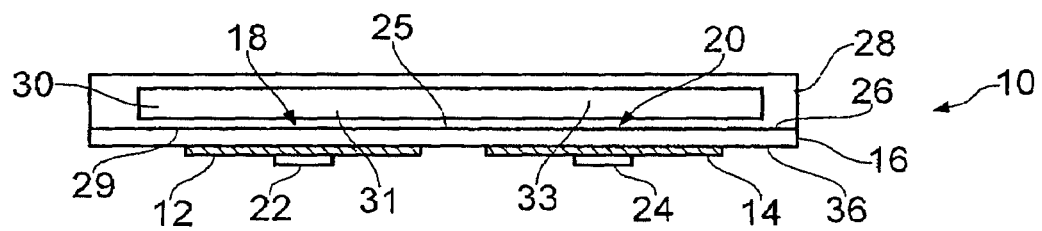
FIG. 2 shows a cross section of the embodiment shown in FIG. 1.

Referring to FIGS. 1 and 2, an embodiment 10 of a heater device to heat a fluid chamber comprises: a first heater 12 and a second heater 14 each disposed on a substrate 16. The first heater 12 has a first heat transfer surface 18 and the second heater 14 a second heat transfer surface 20, each heat transfer surface 18 and 20 are configured to provide thermal contact with a common fluid chamber 30. A first temperature sensor 22 is in thermal communication with the first heater 12. A second temperature sensor 24 is in thermal communication with the second heater 14. It is apparent that the second heater 14 and second temperature sensor 24 are spaced apart from the first heater 12 and the first temperature sensor 24 by a gap 39. The first heater 12 is configured to heat a first region 31 of the fluid chamber; and the second heater 14 is configured to heat a second region 33 of the fluid chamber. In this embodiment the fluid container 28 may be separable from the heater device.

T(time) data is a data set comprising values of a temperature measured by a temperature sensor forming part of the heater device as a function of time. For example, T2 (time) data is such data relating to the second temperature sensor.

Temperature relationship data is data relating estimated values of a temperature Tr at a position within the fluid chamber to values of a temperature sensed at a temperature sensor forming part of the heater device.

Calibration temperature relationship data is a T(time) data set for the situation where the fluid chamber is empty, and is used in a method according to the invention to derive fluid container data and the liquid volume in the chamber.

Liquid data comprises data on properties of the liquid to be used in the fluid chamber, such as heat capacity and thermal conductivity. In some embodiments for example the liquid is a PCR mix.

Liquid volume is the volume of liquid in the fluid chamber. Fluid container data comprises data on the fluid container, such as thermal conductivity and specific heat capacity of the material of the fluid container, thermal conductance and heat capacity of the fluid container itself, and data relating effective thermal properties of the container when containing liquid to those when it is empty. Fluid container data may be provided in a data store forming part of some embodiments of the device relating to specific types of fluid container.

Fluid container identification data comprises data to identify the type of fluid container, such a barcode, RFID or other identification means forming part of the fluid container or packaging associated with it, and may be used to select fluid container data from a data set stored in a data store forming part of the device.

Minimum heating time tmin is the time taken after a step change in temperature T of a heater for the temperature Tr at a location within the fluid chamber to reach to within a chosen range of the new value of temperature T. In a method for controlling a thermocyling process, if Tr is chosen to be the temperature at the centroid of the fluid clamber, tmin is the minimum time for which the fluid container may be held after the first or the second temperature sensor reaches a control temperature Tc before the temperature may be changed to the next temperature in the thermocycle protocol, in order that the liquid has everywhere reached within the chosen range of Tc.

A control temperature Tc is a temperature measured at a temperature sensor forming part of the device at which it is desired that the heater device or a fluid chamber in thermal communication with it may be held.

In some embodiments the first and second heaters are provided on separate substrates, the separate substrates being arranged to contact separate portions of the fluid chamber simultaneously. In some embodiments wherein the fluid container is separable from the heater device the substrates are configured to form surfaces of the receiving location for the fluid container.

Referring to FIGS. 1 and 2, an embodiment 10 of a heater device to heat a fluid container 28 separable from the heater device comprises: a substrate 16 forming a surface of a receiving location 25 for the fluid container, a first heater 12 disposed on a surface 36 of the substrate in thermal communication with a first heat transfer surface 18 within the receiving location, a second heater 14 disposed on a surface 36 of a substrate in thermal communication with a second heat transfer surface 20 within the receiving location, spaced apart from the first heat transfer surface 18, a first temperature sensor 22 in thermal communication with the first heater, a second temperature sensor 24 in thermal communication with the second heater, wherein the receiving location 25 is configured to conform to the fluid container such that the first and the second heat transfer surfaces come into contact with the fluid container.

In this embodiment the first and second heaters are provided on a common planar substrate 16.

In this embodiment the first surface 26 of the substrate 16 provides the receiving location for the fluid container 28 and comprises the heat transfer surfaces. In FIGS. 1 and 2 for simplicity the receiving location 25 is shown as a planar surface; in other embodiments the receiving location may have a different shape, and may comprise location means to position the fluid container at the receiving location, such as the walls of a recess or matching projections and recesses on the fluid container and the substrate, and may comprise retaining means to hold the fluidic container in place at the receiving location, using for example clamping, snap action or friction to hold the container in place. The first and second heaters are both provided on the second surface 36 of the substrate, the first heater comprising a resistive heater track 32 and the second heater a resistive heater track 34, occupying a heated area of a substrate having a perimeter substantially defined by the outer dimensions of the heater track, wherein the first and second heated areas are adjacent and do not overlap, the temperature sensors are mounted on top of the heaters and may be separated from them by an insulating layer. The first and second heaters are connected to a power source by means of contact pads 42, 44 and the first and second sensors are connected to a temperature measurement means via contact pads 46, 48.

The invention is not limited to any specific shape of the fluid container 28. A range of shapes of the heat transfer surfaces 18, 20 and the corresponding surface of the fluid container is envisaged, such that the shapes are configured to allow the heat transfer surfaces to come into thermal contact with the surface of the fluid container. For example the embodiment shown in FIGS. 1 and 2 having a substantially planar format fluid chamber is suitable for use with a planar diagnostic device or a microfluidic device, having a heat transfer surface 29 adapted to engage the heat transfer surfaces 18, 20 of the heater device.

Referring to FIGS. 3 and 4, in a second embodiment 50 the first 12 and second 14 heaters are provided on separate substrates 16a, 16b respectively, the separate substrates being arranged to contact the opposing sides 52, 54 of the fluid container and in use to heat separate portions of the fluid chamber simultaneously, proximal to the sides of the container. In some embodiments the device comprises an insulating layer 40 covering the first and second temperature sensors.

Referring to FIGS. 5 and 6, in a further embodiment 60 in which features common with embodiments 10 and 50 have common numerals, the first heater 12 is provided on the first surface 26a of the first substrate 16a and the first temperature sensor 22 is provided on the second surface 36a within the perimeter of the heated area of the first heater, and the second heater 14 is provided on the first surface 26b of the second substrate 16b and the second temperature sensor 24 is provided on the second surface 36b within the perimeter of the heated area of the second heater. In this embodiment the substrates 16a, 16b provide a region between each heater and the corresponding sensor that has a higher thermal conductance than the thermal conductance of the fluid container plus its contents between the first and the second heaters.

In some embodiments for example as shown, the substrates are planar sheet elements having a first and a second major surface and a thickness between the surfaces less than their width and length. In this embodiment the fluid container 28 may be removable from the heater device, the receiving location 25 being formed by the space between the substrates 16a, 16b. In some embodiments the device comprises an insulating layer 40 substantially or wholly covering the first and second temperature sensors.

Referring to FIG. 7, in further embodiment 70 the substrates 16a, 16b form part of the walls of the fluid chamber 30, the heater device itself being mounted on the housing 72 of the fluid chamber.

Some embodiments as shown in FIGS. 1 to 7 may additionally comprise the following features: An insulation layer 40 may extend substantially over the heater and heated area of each heater as well as over the temperature sensors.

The device may comprise a first thermally conducting layer in thermal contact with the substrate and the first temperature sensor and a second thermally conducting layer in thermal contact with the substrate and the second temperature sensor. Such layers may be provided to increase the thermal conductivity between the sensor and the substrate and/or the heater. Such a layer may comprise for example a layer of copper.

Figure 8:
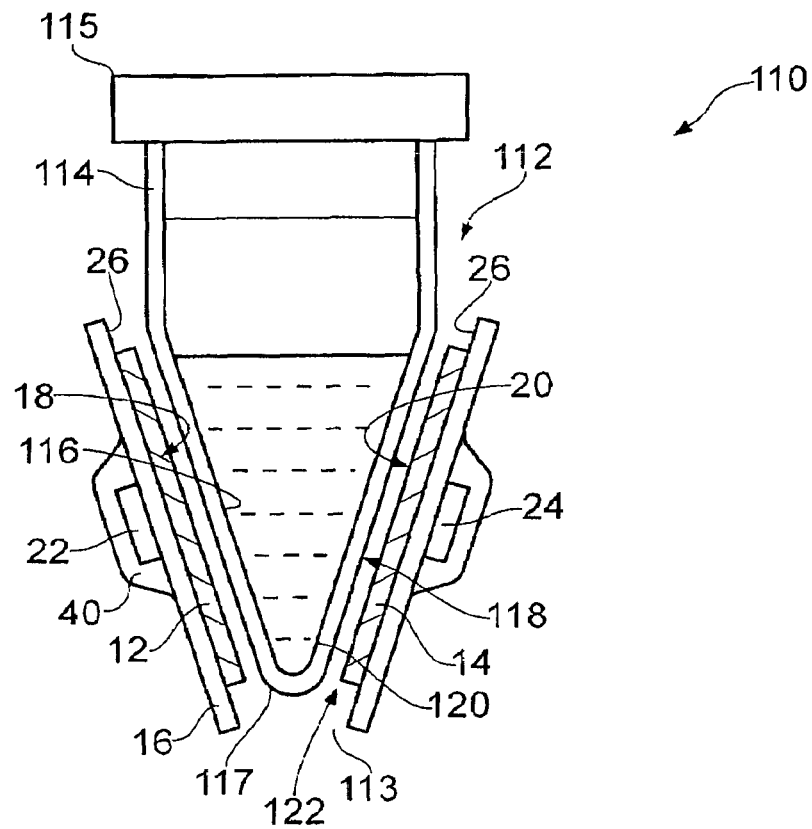
FIG. 8 shows a vertical cross section of a heater device according to the invention with a fluid container in the form of a PCR tube in place within the device.
Figure 9:
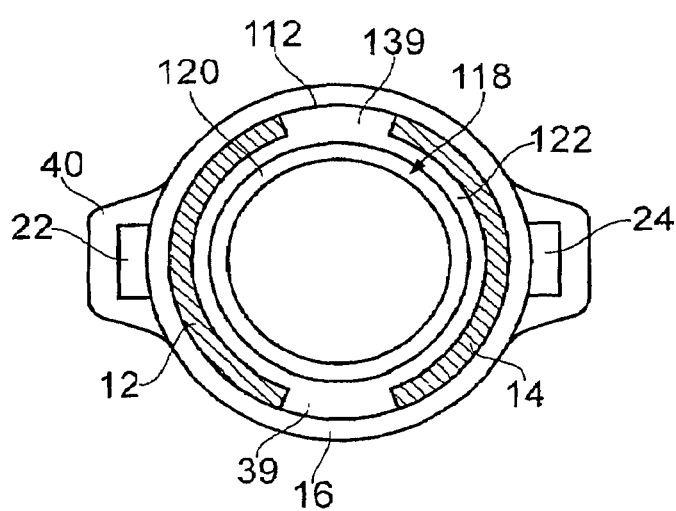
FIG. 9 shows a horizontal cross-section of the embodiment shown in FIG. 8.

Referring to FIGS. 8 to 13, in an embodiment 110 the heater device comprises a receiving location 25 for a fluid container 114 in the form of a recess comprising heat transfer surfaces 18, 20 shaped to contact the fluid container when it is inserted into the heater device. Referring to FIGS. 8 and 9, in this embodiment the heaters 12, 14 are provided on a substrate 16 formed to provide a shaped first surface 26 comprising shaped first and second heat transfer surfaces 18, 20. In this embodiment the first 12 and second 14 heaters are disposed around a recess 112 adapted to receive the fluid container 114.

Recess 112 has a region substantially in the form of as truncated cone to receive a fluid container having a conical portion 116 in its external profile, such as a PCR reaction tube. The recess 112 has a substantially circular horizontal cross section 120 and the second heater 14 is provided at a location diametrically opposed from the first heater 12 and separated from it by gaps 39, 139. The substrate 16 comprises a polymer sheet shaped to form the conical recess, the first surface 26 forming the heat transfer surfaces on the inside of the cone. The heaters are provided on the first surface of the substrate and temperature sensors are provided on the second surface 36 of the substrate within the perimeter of the heated area of each heater.

The cone angle of the recess is preferably selected to match that of the fluid container 114 so as to achieve a close fit of the outside surface 118 of the wall 120 of the fluid container, so as to achieve good thermal contact between the heaters and the fluid container. A conical form is advantageous in use in that the fit of the fluid container to the recess is self-adjusting such that the fluid container will move as far down into the recess as is needed to achieve optimal contact. In general though there will be an air gap 122 between at least a portion of the outside surface 118 and the heat transfer surfaces 18, 20 as shown in FIGS. 8 and 9, and this will add to an effective heat transfer resistance between the heaters 12, 14 and the wall 120 of the fluid container.

It will be apparent that other shapes of receiving location or recess are within scope of the invention, such as tapered or uniform in cross-section, cylindrical, having a planar, conical or curved base, rectilinear or a combination of such shapes to conform to the shape of a wall of a fluidic container. The recess may be open at the base 113 or closed, and may comprise an opening adapted to channel gas flow over the fluid container, for example for convection cooling in a thermo cycling application.

Figure 10:
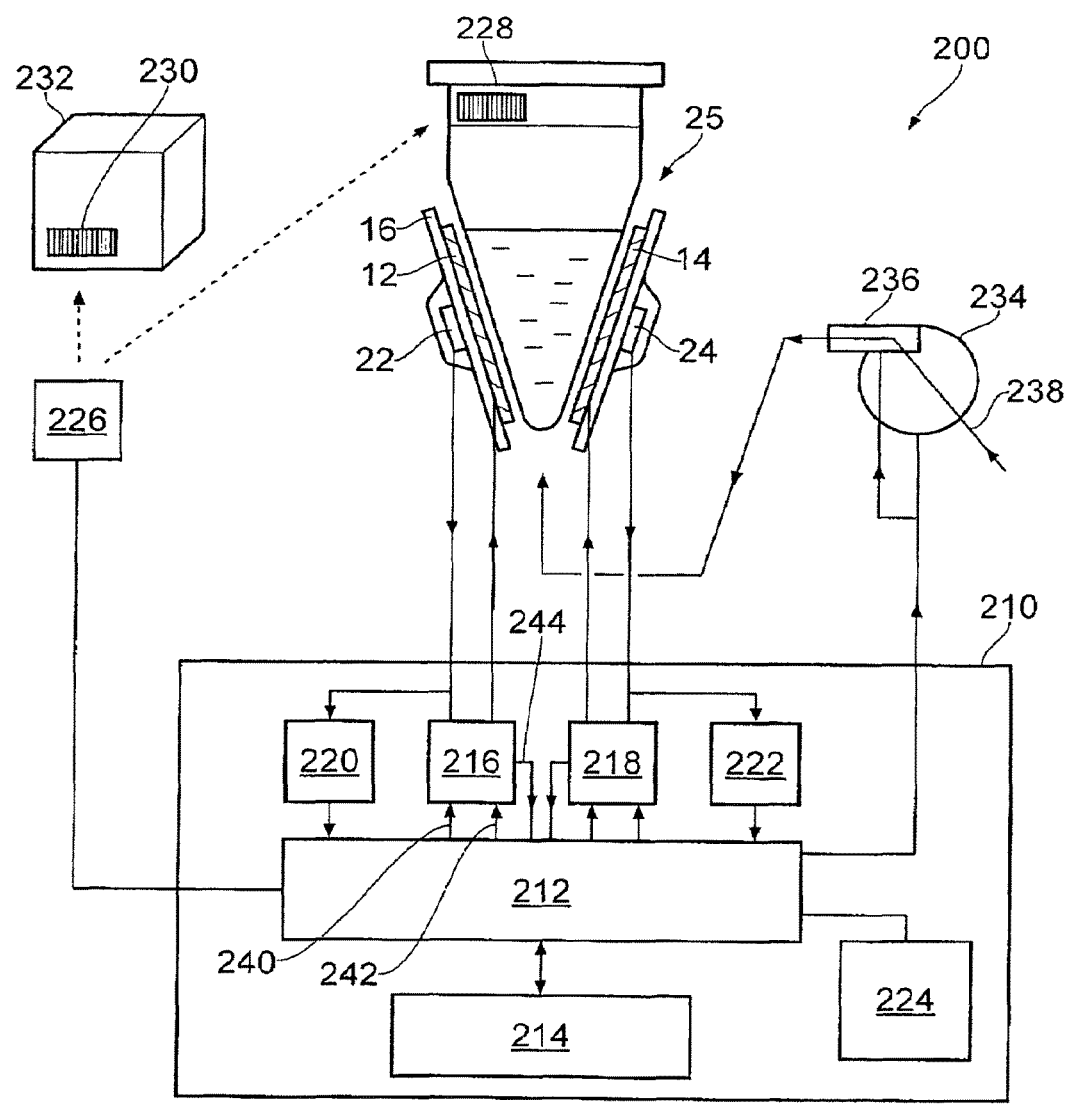
FIG. 10 shows a block diagram of an embodiment of the invention.

Referring to FIG. 10, an embodiment 200 of a heater device further comprises a control means 210 adapted to control the first heater 12 using data from the first temperature sensor 22 and to control the second heater 14 using data from the second temperature sensor 24, each heater being controlled independently of the other.

The control means comprises a computer 212, a data store 214, a control program running on the computer, a user interface 224 for data output and input, a first heater control means 216 adapted to control the first heater 12 using data from first temperature sensor 22, a second heater control means 218 adapted to control the second heater 14 using data from second temperature sensor 24, and a first 220 and second 222 sensor temperature reading means. The computer 212 is adapted to receive data from the sensor temperature reading means and to send control data to the heater control means, for example to set heater power on/off (shown as data flow arrow 240) and to set the heater temperature (242) and to receive data on the heater power (244) from the heater control means. The heater control means 216, 218 may comprise a software routine forming part of the control program or may comprise a separate subsystem configured to control the heaters and to receive command data from the computer. The control means is configured to receive data from a data reader 226, here shown as a barcode reader, for example identification data 228 associated with the fluid container or 230 associated with another source, for example packaging 232 for the fluid container.

In some embodiments the heater device comprises a fan 234 and optionally a cooling means 236 to provide convection cooling to the heater device and the fluid container and control means is adapted to control the fan and cooling means. The airflow pathway 238 is provided according to the embodiment, for example with the heater device 110 airflow is advantageously from below to cool the device and the fluid container uniformly.

According to the embodiment the control means is configured to carry out one or more processes and steps in a method of the invention as described herein. Preferably the control means comprises a control program comprising routines to carry out the one or more processes and steps forming part of the method and algorithms to derive the one or more quantities and values described herein.

Figure 11:
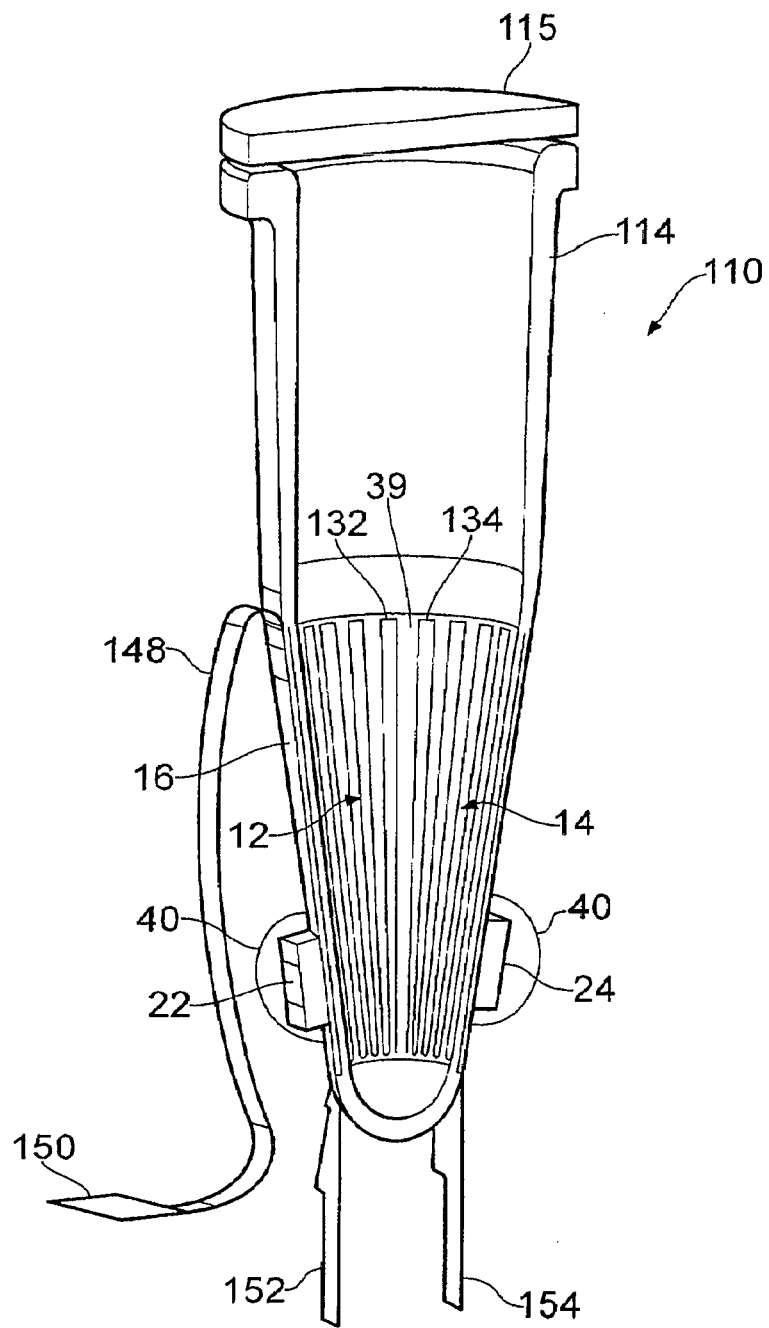
FIG. 11 shows a vertical cross section of an embodiment as shown diagrammatically in FIG. 8 in which the substrate comprises a formed polymer sheet.
Figure 12:
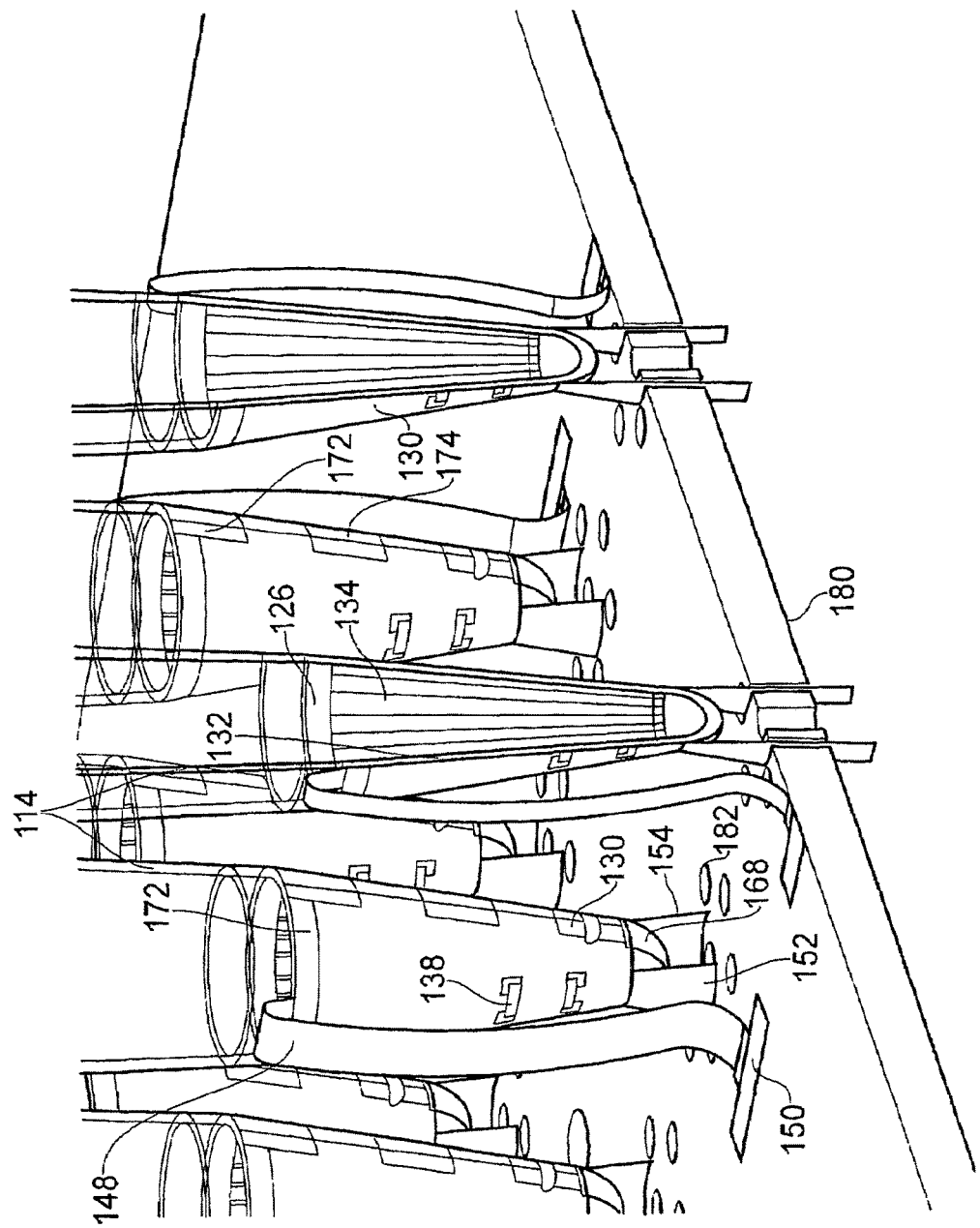
FIG. 12 shows a cut-away isometric view of part of an apparatus comprising a plurality of heater devices as shown in FIG. 11.
Figure 13:
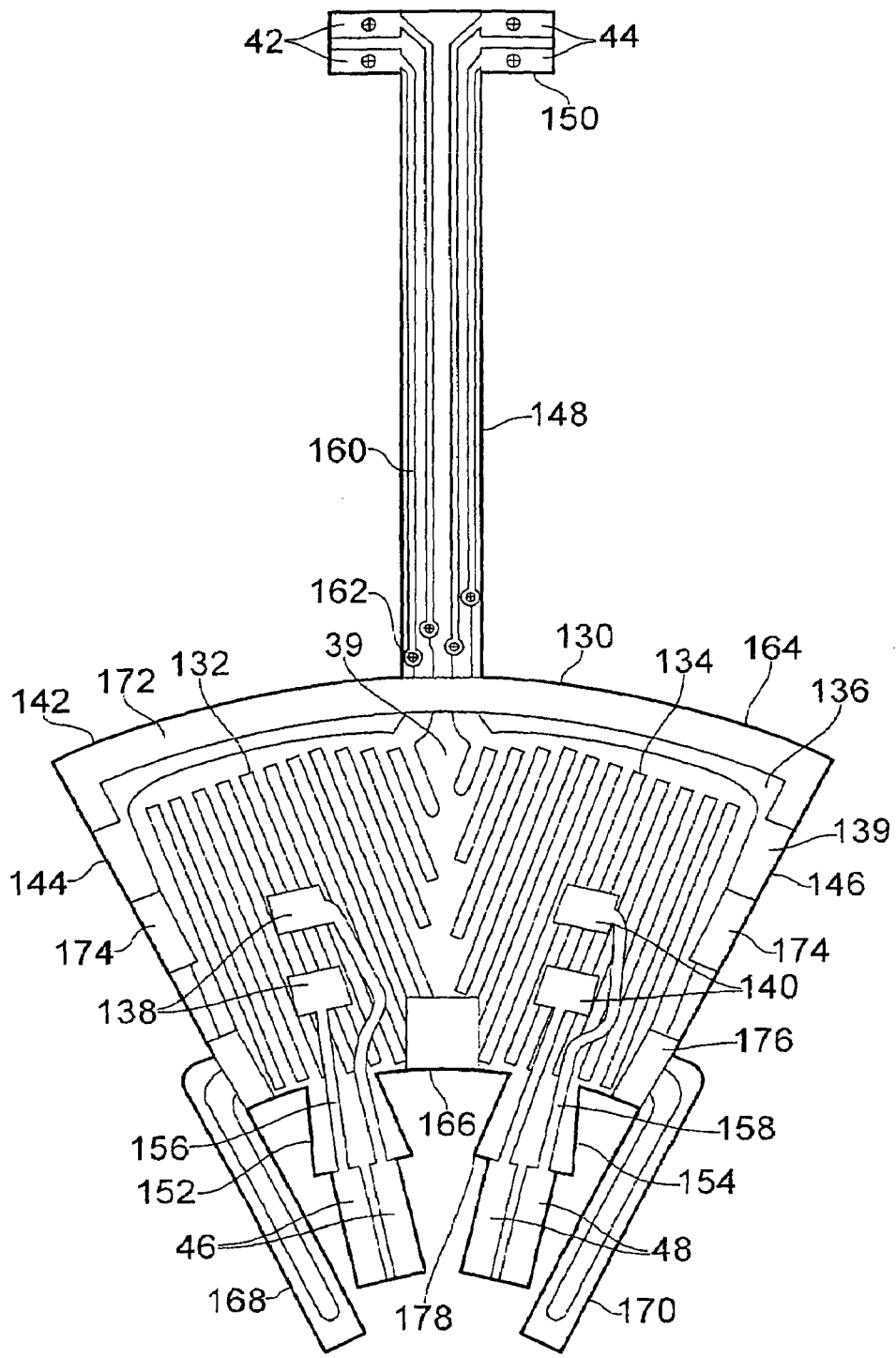
FIG. 13 shows a substrate formed from a polymer sheet as may form part of an embodiment of the invention as shown in FIGS. 11 and 12.
Figure 14:
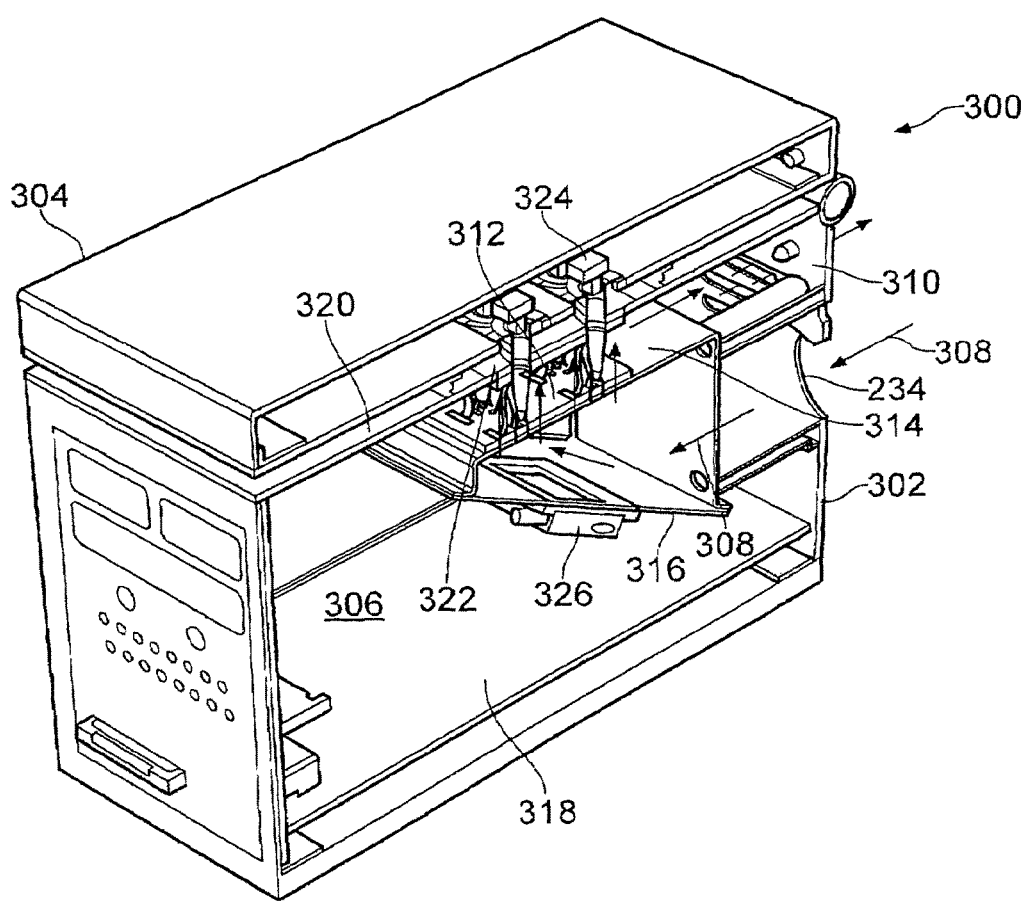
FIG. 14 shows a cut-away isometric view of an embodiment of a thermocycler apparatus according to the invention.

Referring to FIGS. 11 to 13, the embodiment 110 is further illustrated. The substrate 16 comprises a flexible polymer sheet form 130 shaped to form a truncated conical recess when assembled, the sheet form comprising an arcuate portion 142, and having on a first surface 126 forming the inside of the conical recess a first heater 12 comprising a first serpentine resistive track 132 and a second heater 14 comprising a second serpentine resistive track 134 spaced apart from the first by a gap 39, and on the second opposing surface 136 of the sheet form, which forms the outside of the conical structure when assembled, a first pair of contacts 138 for a first temperature sensor 22 and a second pair of contacts 140 for a second temperature sensor 24. The view in FIG. 13 is with the second surface 136 uppermost, the polymer substrate being illustrated as being transparent so that the heater tracks may be seen through it.

Polymer sheet form 130 comprises an arcuate portion 142 configured to position its first surface comprising the heat transfer surfaces inside a conical recess when the arcuate portion is rolled up and joined along the edges 144 and 146; an elongated lead portion 148 extending from external arc edge 164 of the arcuate portion and carrying conductor tracks 160 connected to the heater tracks 132, 134 to first heater contacts 42 and second heater contacts 44, provided on a contact pad portion 150 of the polymer form 130. When the polymer form is assembled, a second gap 139 between the heaters is formed at the join between the edges 144 and 146.

In this embodiment, the heater resistive tracks 132, 134 are provided on the first surface of the substrate and the heater contact tracks 160 are led to the second surface by means of vias 162, such that when the lead portion 148 is bent over in a loop as shown in FIG. 12 the heater contacts 42 and 44 are on the lower side of contact pad portion 150 to make contact with conductor track on the upper side of the supporting PCB 180. The polymer form further comprises first 152 and second 154 tabs extending from the internal arc edge 166 of the arcuate portion and carrying conductor tracks 156, 158 to the first temperature sensor contacts 46 and the second 48.

In this embodiment the sheet form 130 further comprises projections 168 and 170 on which a portion of the heater tracks are provided, and which are shaped to extend underneath the lower opening 113 of the conical recess 112 formed by the polymer form 130 and to be joined together to form a loop underneath the lower opening as shown in FIG. 12, so as to heat the lower rounded conical end portion 117 of a conical fluid container placed in the recess. Such projections are optional and in some embodiments are not present. The polymer sheet form 130 further comprises metallised regions 172, 174 and 176 that provide means to bond the edges 144 and 146 of the arcuate portion 142 into a conical form. The metallised region 172 extending around the upper rim of the conical recess when formed may act to stiffen the upper edge so providing a robust structure.

Referring to FIG. 12, a plurality of the heater devices 110 are shown mounted on a circuit board 180 with the tabs 152 and 154 extending through holes in the circuit board and acting to support the devices. The tabs are provided with a shoulder 178 to engage the upper surface of the circuit board to support the device. The heater contact tab 150 is shown soldered to the upper surface of the circuit board. In this way the heater device may be provided in multiple in a cost-effective and robust manner, allowing it to be used in a multi-channel thermo cycling apparatus as described herein. The circuit board 180 comprises one or more apertures 182 through it adjacent to the heater devices adapted to provide a gas flow pathway through the circuit board such that gas flowing through the apertures impinges on the substrate, so acting to cool the substrate. In some embodiments a plurality of apertures are provided, in this embodiment four apertures, at least a portion of the apertures being vertically below a portion of the substrate.

Referring to FIGS. 14, 15a, 15b and 16, an embodiment 300 of the invention is an apparatus to run multiple reactions in parallel, for example in thermo cycling reactions such as for PCR, comprising a plurality of heating devices as described herein and a control means configured to control the heating devices independently.

Figure 15A:
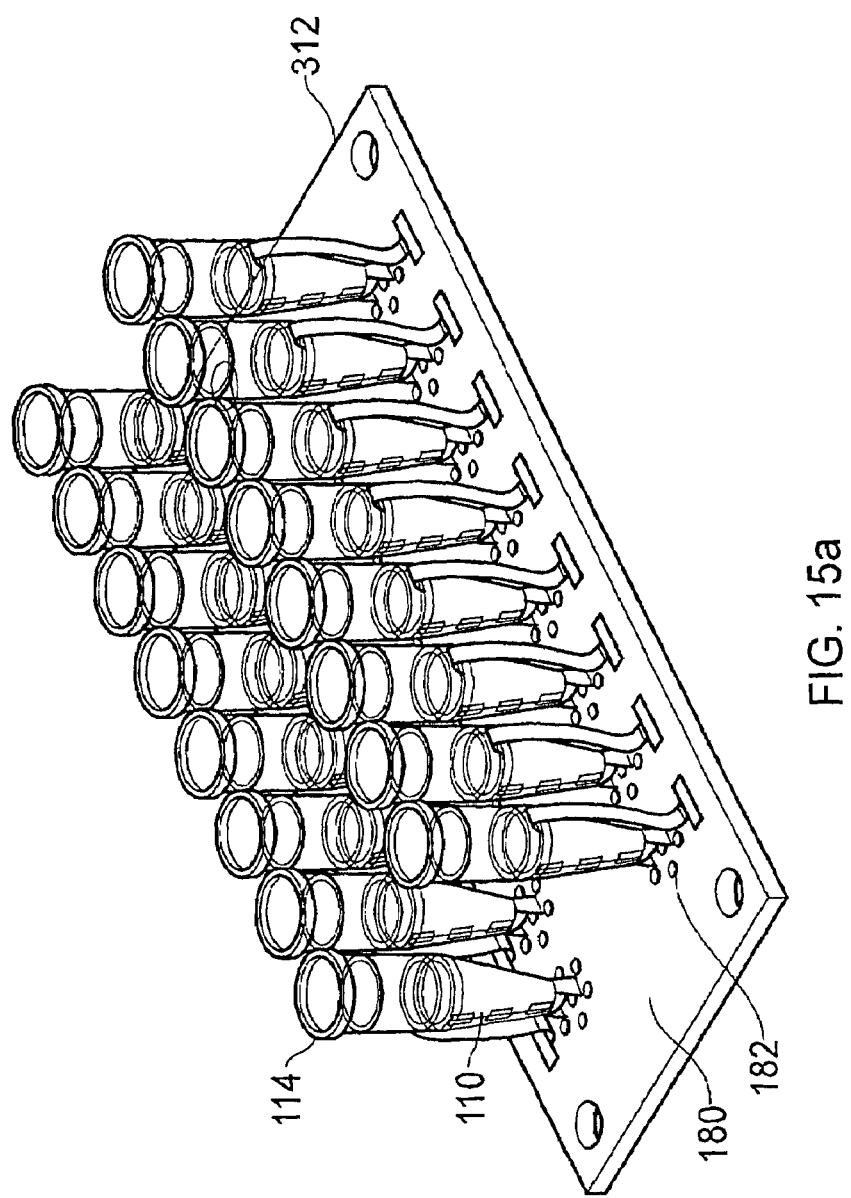
FIG. 15a shows an isometric view of part of an apparatus comprising a plurality of heater devices as shown in FIGS. 11 and 12 suitable for use in the embodiment in FIGS. 14 and 16.
Figure 15B:
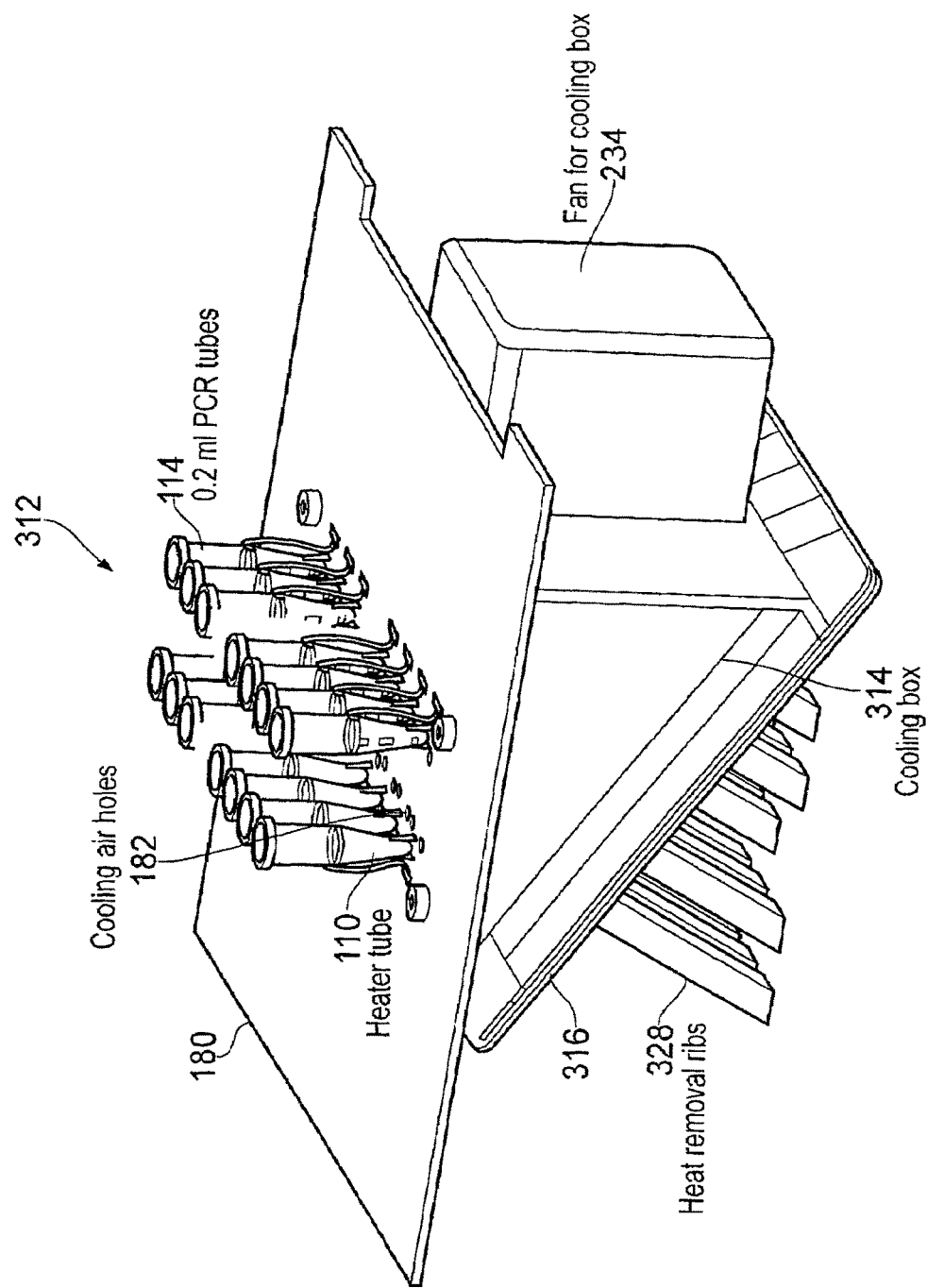
FIG. 15b shows an isometric view of a subassembly of an apparatus comprising a plurality of heater devices as shown in FIGS. 11 and 12 suitable for use in the embodiment in FIGS. 14 and 16.
Figure 16:
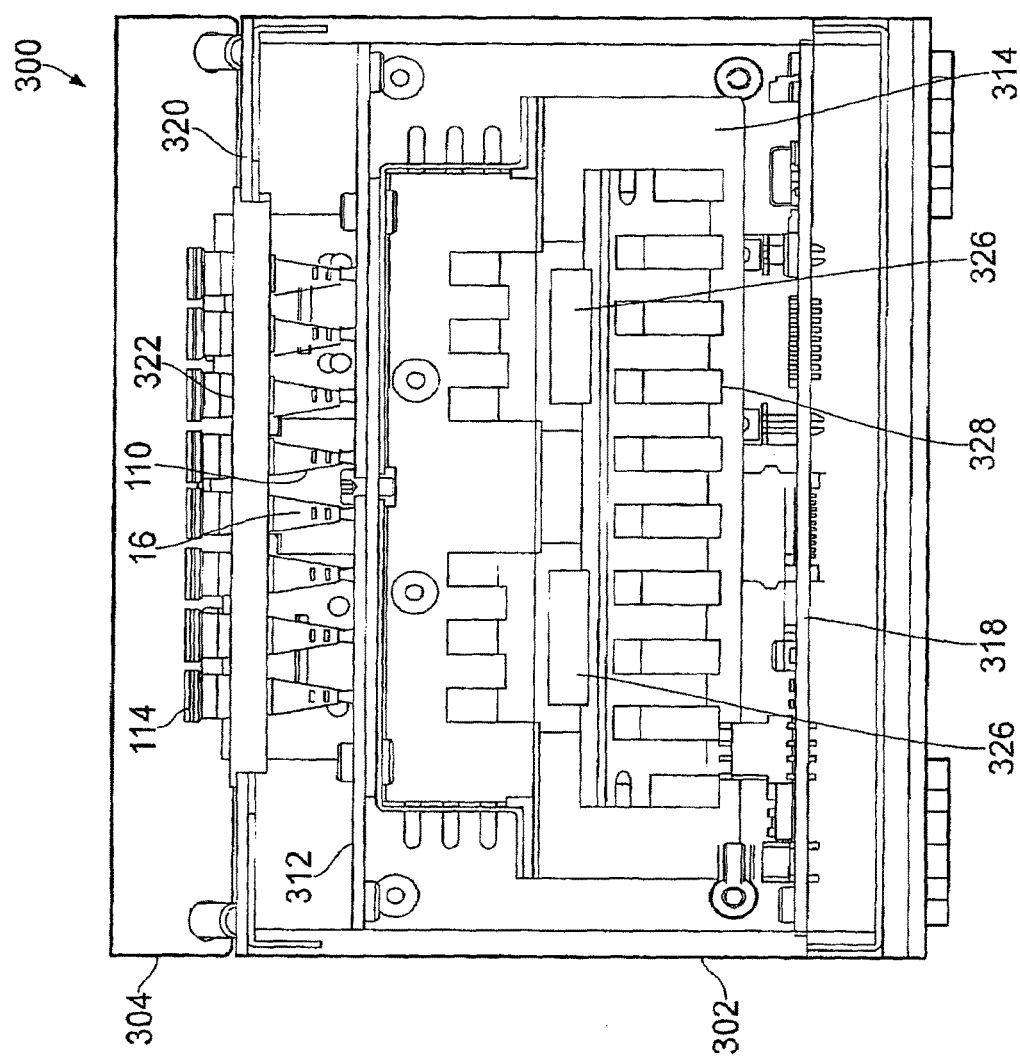
FIG. 16 shows a cross section of an embodiment of a thermocycler apparatus as shown in FIG. 14.

In this embodiment the apparatus 300 comprises: a housing 302 having a lid 304 to define an interior space 306, a plurality of separate heater devices 110 as described herein located within the housing and thermally isolated from each other, each being configured to receive a separate removable fluid container 114, a control means 210 configured to control each heater device independently, an air flow means within the housing adapted to cause airflow over the heater devices, here comprising a fan 234 (only the edge of the fan is shown in the cutaway illustration of FIG. 15a), wherein the lid 304 is openable to place the fluid containers 114 into thermal contact with the heater devices 110 and closable to define an interior space enclosing the fluid containers.

In this embodiment the fluid containers 114 are reaction tubes, such as PCR tubes and the heater devices 110 comprise a recess 112 to receive the fluid containers.

In this embodiment the apparatus comprises an air flow means to direct air over the surface of a heater device and over a fluid container when in thermal contact with the heater device, comprising a fan 234 and an air flow pathway 308 within the housing to direct the air flow from the fan through a cooling means and to an air outlet 310, passing over the heater devices to control the rate of convection heat dissipation from the heater device and the fluid container.

In this embodiment the airflow serves primarily to provide rapid cooling of the heater devices and the fluid containers. In some embodiments the airflow is provided while the heaters are powered to ensure improved control over the rate of convection heat loss, which without the forced air flow would depend on natural convection and so would tend to be subject to greater variation, in particular depending on the temperature of the heater device and fluid container. The air flow speed may be controlled by the control means to be greater during a cooling phase of a thermo cycling reaction and lesser, or zero, during a heating phase.

The apparatus 300 comprises a heater device array 312 comprising a plurality of heater devices 110 adapted to receive PC R tubes 114, mounted on a circuit board 180, the heater devices here being in two parallel rows of eight devices to run sixteen reactions in parallel. The apparatus comprises a cooling unit 314 comprising a baffle 316 supporting one or more Pettier cooling devices 326 cooling the air volume inside unit 314 through which the air flow pathway 308 passes, then passing through the apertures 182 adjacent to each heater device 110, to provide an airflow pathway over the heater devices and the fluid containers, then venting through vent 310. The Peltier devices sink heat to heat sinks 328, which may also be provided with a cooling airflow from a fan, for example the same fan 234.

The control means 210 is provided on a circuit board 318 together with other circuitry as may be required such as a power supply. The apparatus comprises a fascia 320 supporting a heater device support block 322 adapted to hold and to reinforce the upper part of the conical substrate 16. Further components of the apparatus include a fluid container detection switch 324 that is actuated when a PCR tube is in place in the heater device.

The apparatus 300 may be operated in connection with a user interface, for example comprising an external computer or display, and the control program for the control means may in some embodiments run on an external computer, commands being passed to the control means using a data link. For example, lower level operating programs for the apparatus may run on the control means, and a higher level program may run on an external computer to provide a user interface as known in the art.

The heater device substrate may be formed from a thin polymer film as used in microelectronics, for example a polyimide film. The device may be sized to suit a chosen fluid container, or a range of chosen containers. For example, to suit a standard PCR tube the polymer film form 130 may have substantially the following dimensions: arcuate portion 142, radially from inner edge 166 to outer edge 164: 9.54 mm; overall dimension from outer edge 164 to the end of projection 170: 15.5 mm; angle of edges 144 and 146 one to another: 53.1 degrees; length of the elongated lead portion 148: 14.9 mm.

The temperature sensors may comprise Pt1000 type sensors in a surface mount package, the contacts 138 and 140 being spaced apart and sides to accommodate the dimensions of the package. The heater and contact tracks may be formed using standard electronic fabrication techniques as known in the prior art. The substrate in some embodiments is a flexible PCB film as known in the art, for example formed from polyimide. In an embodiment such as embodiment 110 the film is of the order 100 um thick. The film may be reinforced by means of metal areas as shown for example in FIG. 13, which act to stiffen the film in areas such as the perimeter of the opening to the recess. When formed and the edges are bonded together, the truncated conical form of the heater device provides a strong and durable structure suitable for repeated use with a removable PCR tube.

FIGS. 17 to 22 show flow diagrams for methods of the invention to carry out processes involving heating of a fluid chamber by the heater device as described herein. In some embodiments the control means comprises a control program adapted to carry out one or more of these steps.

Figure 17:
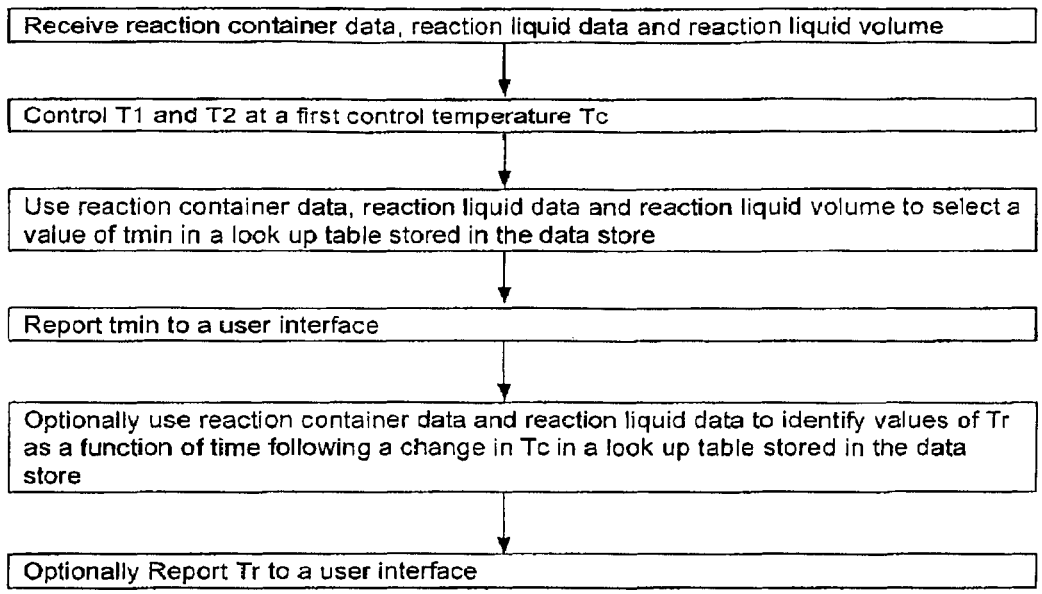
FIG. 17 shows the steps in a method according to the invention.

FIG. 17 shows a method to heat a fluid chamber using a value of tmin, the minimum heating time for equilibration in the fluid chamber and/or Tr inside the fluid chamber, derived using a lookup table in the data store.

Figure 18:
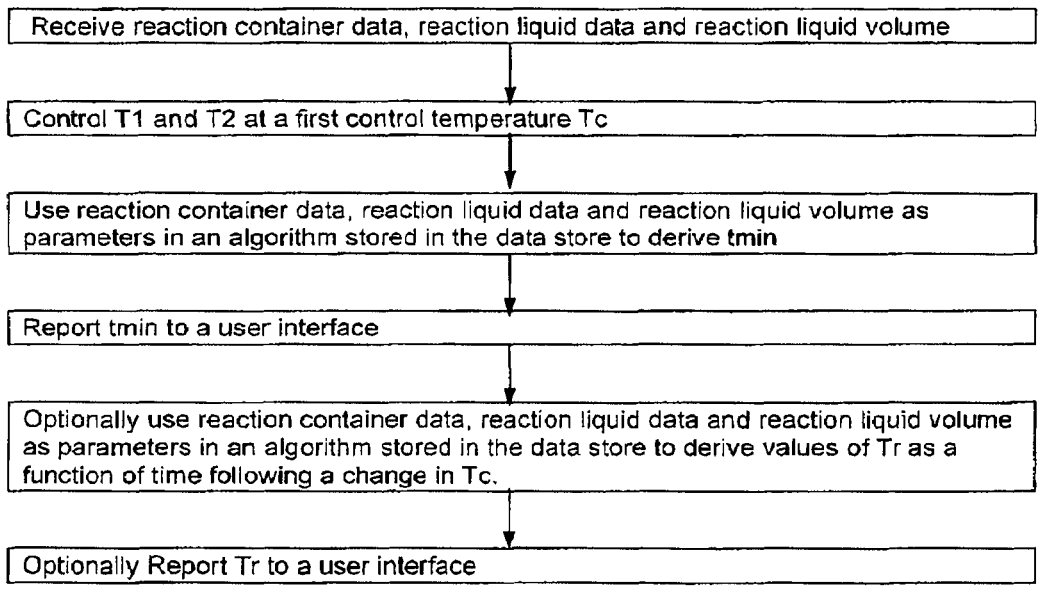
FIG. 18 shows the steps in a further method according to the invention.

FIG. 18 shows a method to heat a fluid chamber using a value of tmin, the minimum heating time for equilibration in the fluid chamber and/or Tr inside the fluid chamber, derived using an algorithm to calculate one or both parameters.

Figure 19:
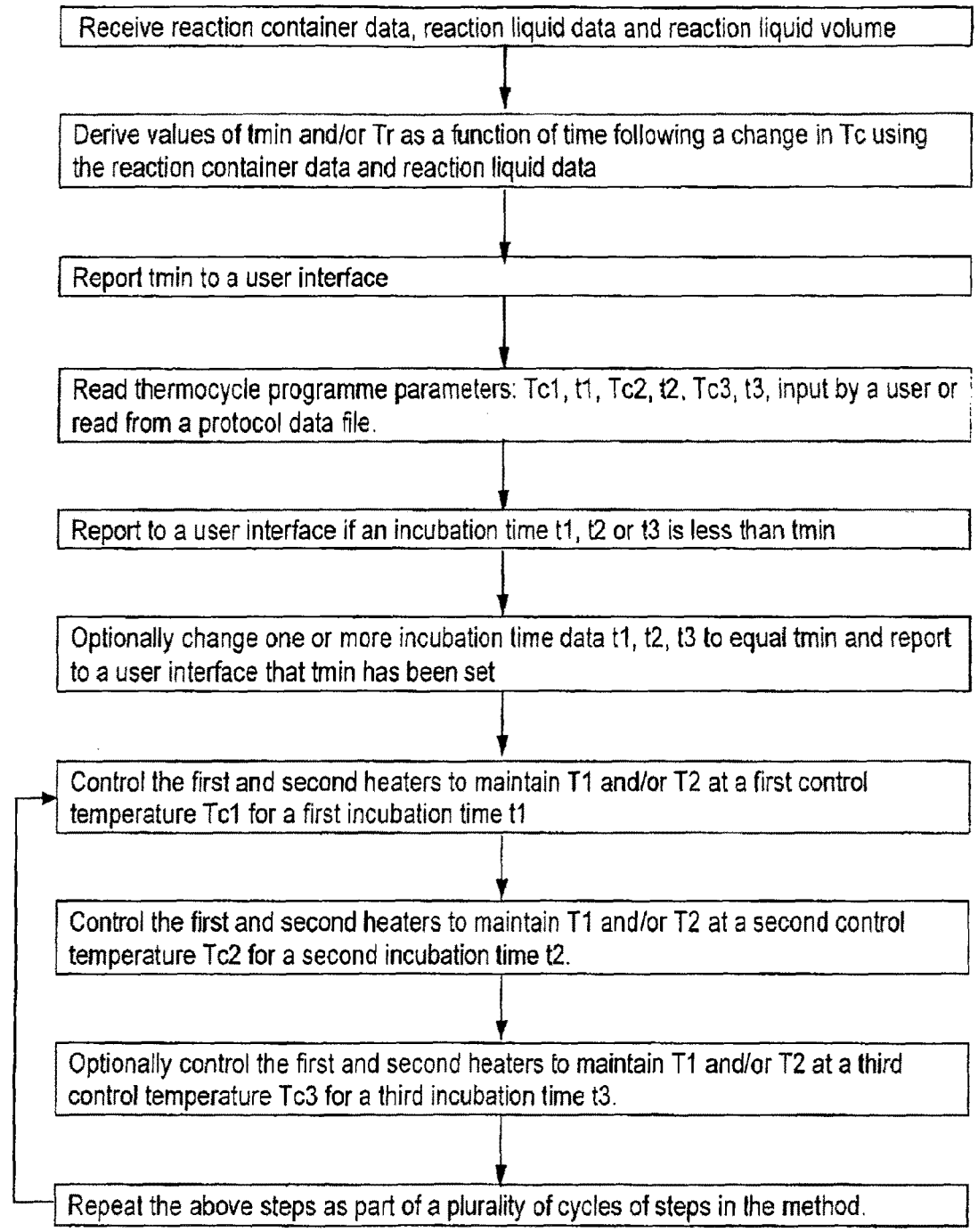
FIG. 19 shows the steps in a further method according to the invention.

FIG. 19 shows a method to control a thermo cycler device as described herein.

Figure 20:
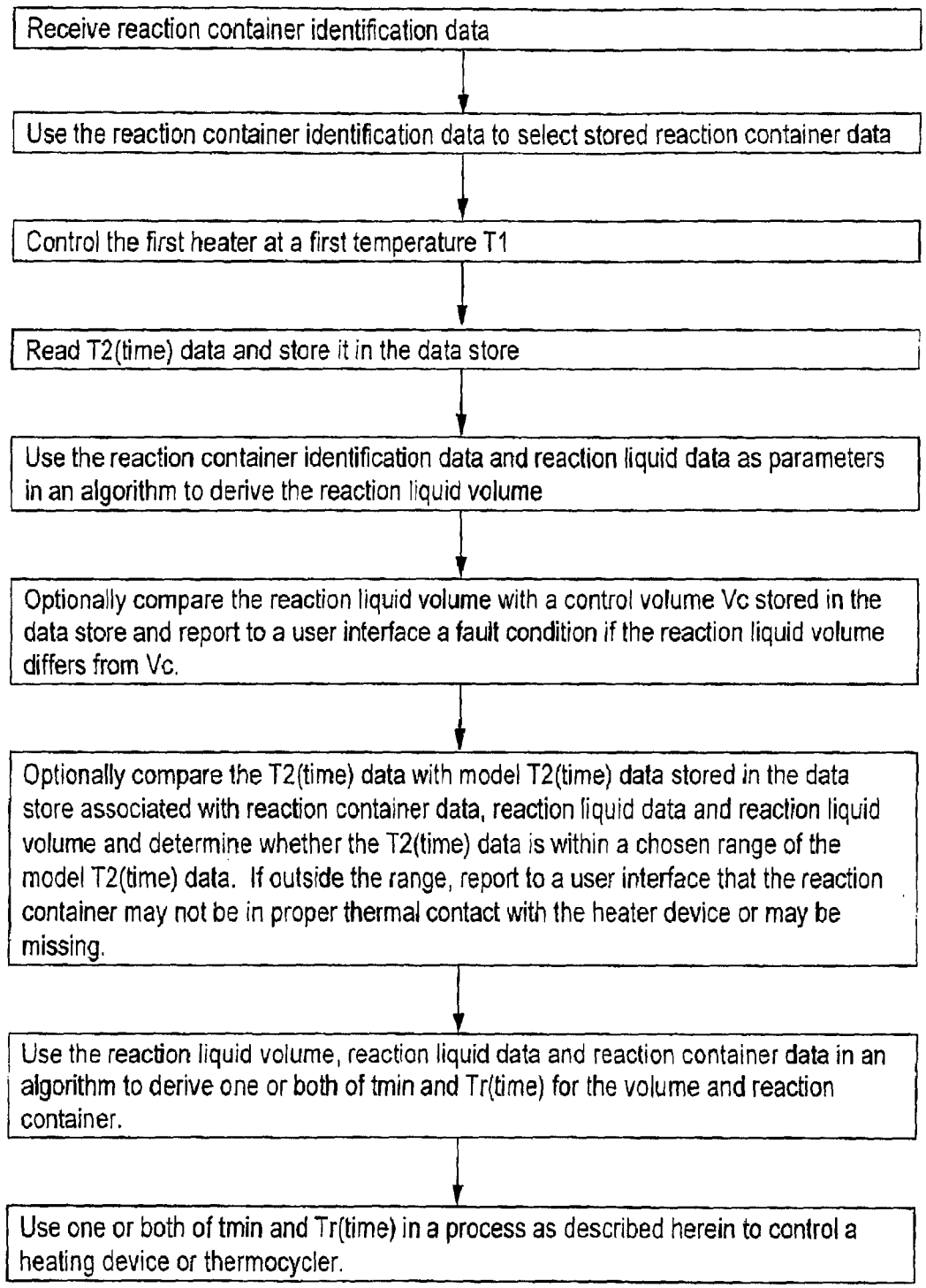
FIG. 20 shows the steps in a further method according to the invention.

FIG. 20 shows a method to derive the liquid volume in a fluid chamber or to indicate a poor level of filling, or to check for poor thermal contact between a removable fluid container and the heater devices.

Figure 21:
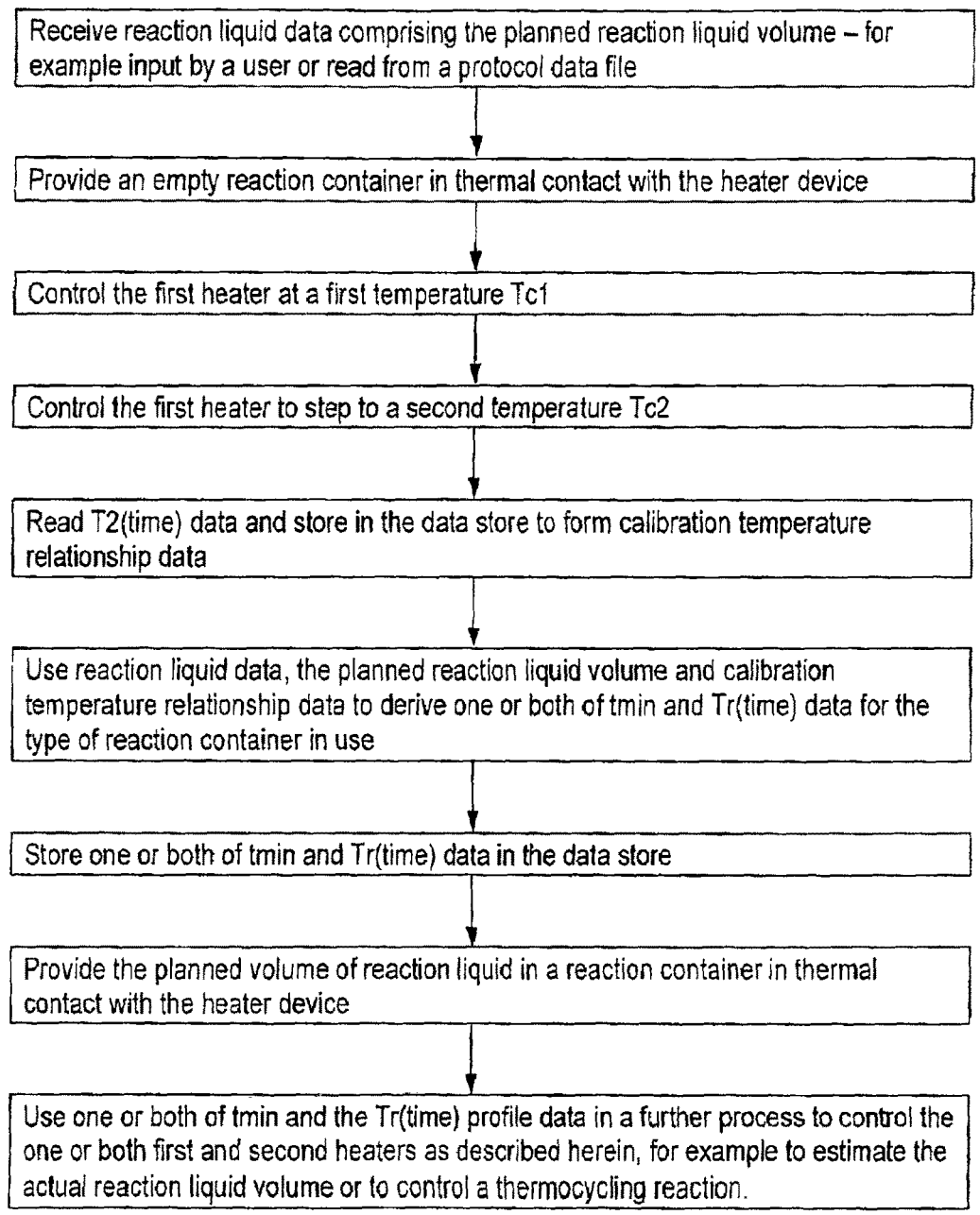
FIG. 21 shows the steps in a further method according to the invention.

FIG. 21 shows a method to calibrate the heater device or a thermo cycler device incorporating it in the case that a non-standard fluid container is used, but the control liquid volume, i.e. the volume of liquid to be added to the, or each fluid chamber, is known.

Figure 22:
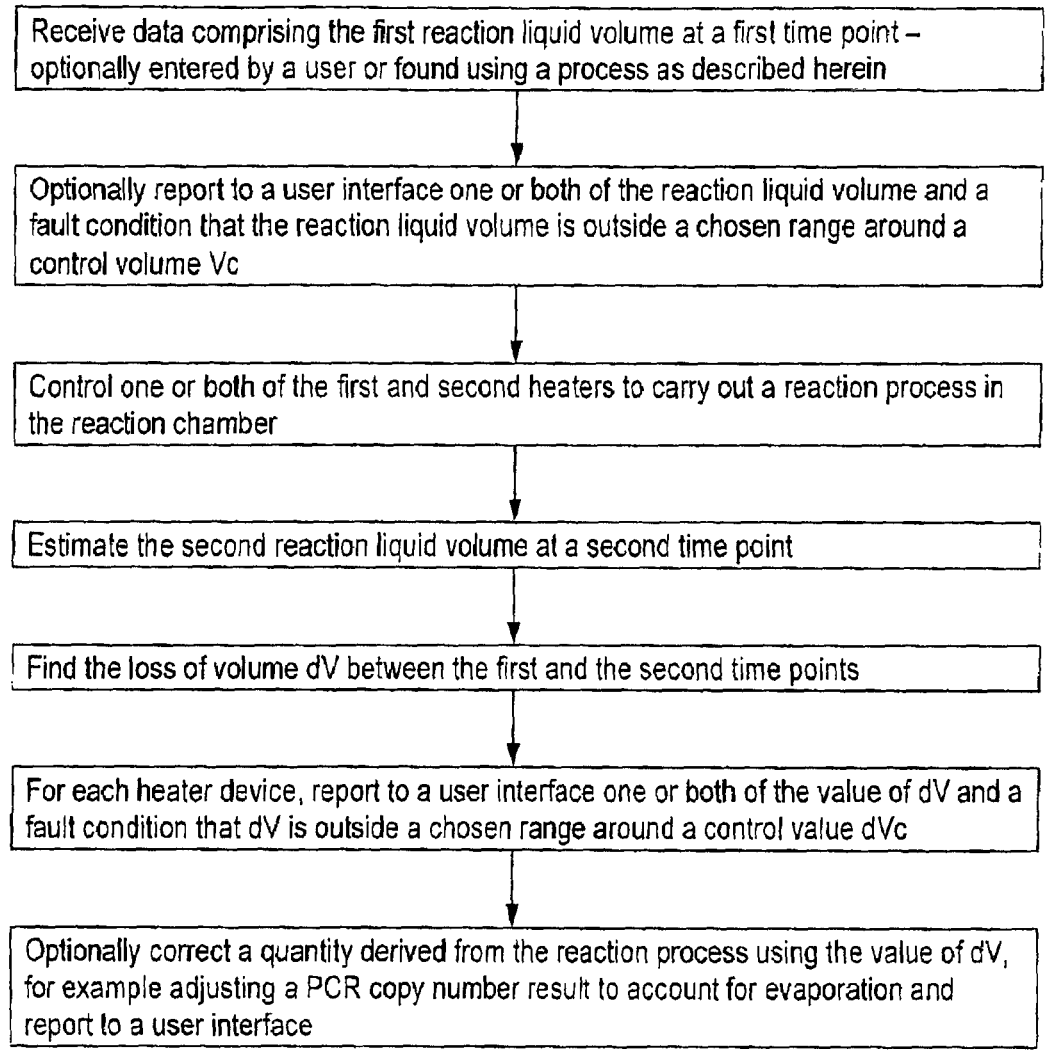
FIG. 22 shows the steps in a further method according to the invention.
Figure 23:
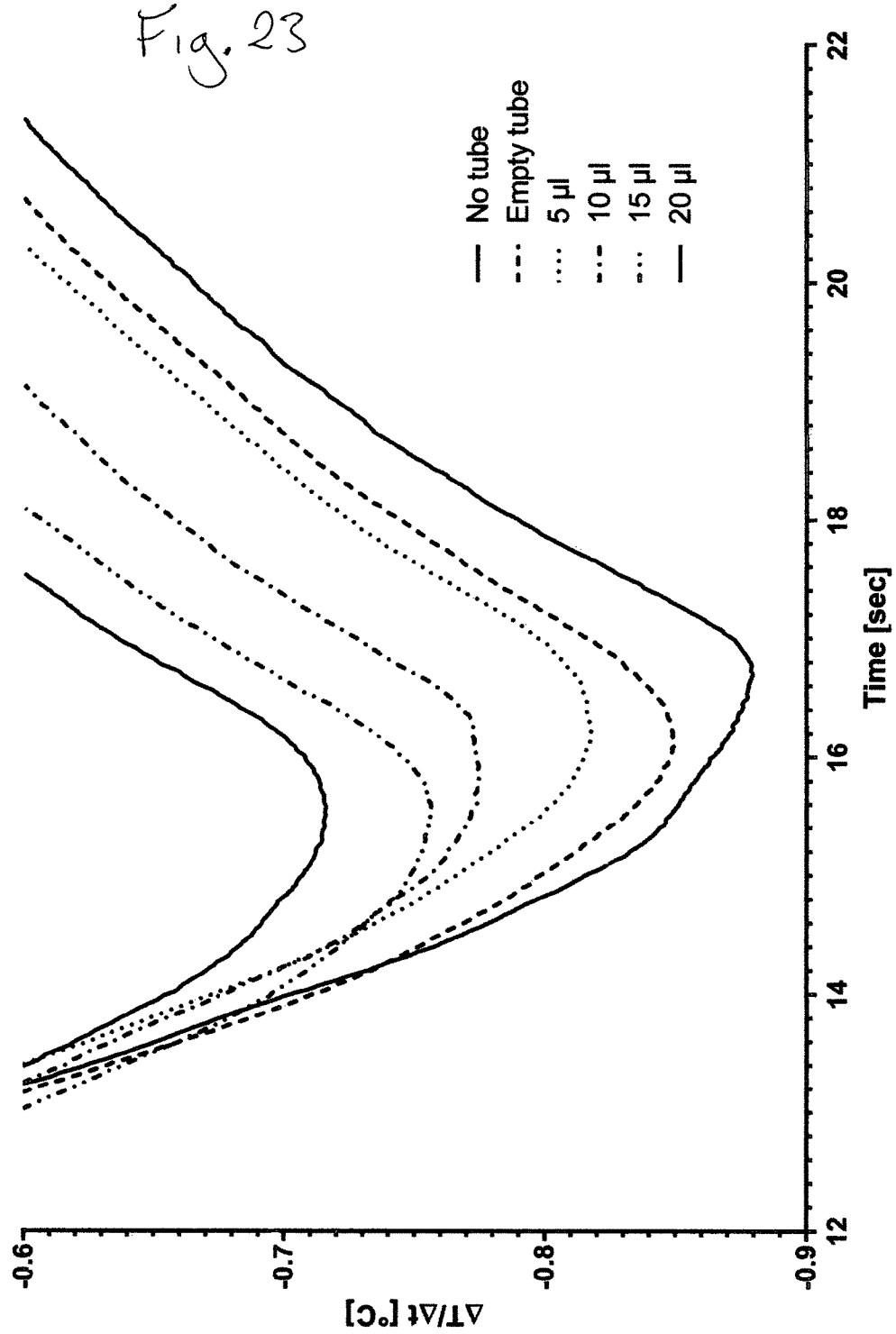
FIG. 23 shows graphs of cooling curves for a pulse of energy sufficient to provide a 20° C. temperature rise in an empty fluid container and fluid containers with differing volumes of liquid.

FIG. 22 shows a method to derive a volume of a liquid and to monitor a reaction process where volume may be lost through evaporation.

Algorithms for use in embodiments of the invention suitable for use with the embodiment 110 may comprise the following:

Modelling of thermal diffusion into a volume of liquid having a truncated conical form from a uniform temperature at the conical surface with no heat transfer at the ends;

Modelling of heat transport from a first temperature distribution at a first portion of a conical surface to a second temperature distribution at an opposing portion of the surface, and temperature distribution within the liquid;

Modelling as above assuming that (i) the portions are approximated by a hemi-conical surface and/or (ii) the temperature distributions are uniform.

Modelling of heat transport within the structure of an empty fluid container in contact with a first heater at a first portion of the conical surface of the container to a heat sink at an opposing side of the container.

Modelling of heat loss to convection from the heater device and/or the heated fluid container.

The invention has been described by way of examples only and it will be appreciated that variation may be made to the above-mentioned embodiments without departing from the scope of invention.

With respect to the above description then, it is to be realised that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the claims.

The invention claimed is:

1. A heater device to heat a fluid container separable from the heater device comprising:
   one or more substrates each forming a surface of a receiving location for the fluid container,
   a first heater disposed on a surface of a substrate in thermal communication with a first heat transfer surface within the receiving location,
   a second heater disposed on a surface of a substrate in thermal communication with a second heat transfer surface within the receiving location spaced apart from the first heat transfer surface,
   a first temperature sensor in thermal communication with the first heater,
   a second temperature sensor in thermal communication with the second heater, and
   a control means adapted to control the first heater using data from the first temperature sensor and to control the second heater using data from the second temperature sensor, each heater being controlled independently of the other,
   wherein the receiving location is configured to conform to the fluid container such that the first and the second heat transfer surfaces come into contact with the fluid container; and
   wherein the control means has a first mode of operation in which it controls both heaters to heat the fluid chamber simultaneously, and a second mode in which it controls the first heater to heat the fluid chamber and measures the temperature of the second sensor against time.

2. A device according to claim 1 wherein in the second mode the control means controls the first heater to change from a first to a second constant temperature at the first sensor while measuring the temperature of the second sensor against time.

3. A device according to claim 1 wherein each heater comprises an extended resistive heater track.

4. A device according to claim 1 wherein the first and second heaters are disposed around a recess adapted to receive the fluid container and the first and second heat transfer surfaces are provided within the recess.

5. A device according to claim 4 wherein the recess has a substantially conical region to receive a fluid container having a conical portion of its external profile.

6. A device according to claim 4 wherein the recess has a substantially circular horizontal cross section and the second heater is provided at a location diametrically opposed from the first heater.

7. An apparatus comprising a plurality of heating devices according to claim 1 and a control means configured to control the heating devices independently.

8. An apparatus according to claim 7 comprising a thermocycling device configured to run a plurality of independent thermocycling reactions in parallel and to measure a quantity of or within the liquid, for example from the list of: liquid volume, absorbance, fluorescence, turbidity, optical activity (polarisation), conductivity, temperature, pH.

9. An apparatus according to claim 8 configured to measure a quantity within the liquid and the liquid volume at a first time point before or during a reaction process, and again at a second time point later in the reaction process or after the process ends, and to use the measurement of the liquid volume to change a reported value of the first quantity.

10. An apparatus according to claim 8 configured to correct a first quantity for evaporation, in which the evaporated volume is found from an estimate of the liquid volume before and after the reaction.

11. A heater device according to claim 1, wherein the heater has a temperature coefficient of resistance and the temperature sensor comprises the heater.

12. A heater device according to claim 1, wherein the thermal conduction pathway from the first heater to the first temperature sensor has a greater thermal conductance than that from the first heater to the second sensor and the thermal conduction pathway from the second heater to the second temperature sensor has a greater thermal conductance than that from the second heater to the first sensor.

13. A heater device according to claim 1, wherein the first temperature sensor is provided on a surface of the substrate closer to the first heater than to the second heater and the second temperature sensor is provided on a surface of the substrate closer to the second heater than to the first heater.

14. A heater device to heat a fluid container separable from the heater device comprising:
   one or more substrates each forming a surface of a receiving location for the fluid container,
   a first heater disposed on a surface of a substrate in thermal communication with a first heat transfer surface within the receiving location,
   a second heater disposed on a surface of a substrate in thermal communication with a second heat transfer surface within the receiving location spaced apart from the first heat transfer surface,
   a first temperature sensor in thermal communication with the first heater,
   a second temperature sensor in thermal communication with the second heater, and
   a control means adapted to control the first heater using data from the first temperature sensor and to control the second heater using data from the second temperature sensor, each heater being controlled independently of the other,
   wherein the receiving location is configured to conform to the fluid container such that the first and the second heat transfer surfaces come into contact with the fluid container;
   wherein the device is adapted to carry out a thermocycling reaction within the fluid chamber, the control means being configured to:
   derive a minimum heating time tmin as described herein,
   control one or both of the first and the second heaters to heat the fluid chamber until one of T1 and T2 reaches a first chosen control value Tc1, control one or both of the first and the second heaters to maintain one of T1 or T2 within a chosen range of Tc1 for a time t1, control one or both of the first and the second heaters to heat the fluid chamber until one of T1 and T2 reaches a second chosen control value Tc2, and control one or both of the first and the second heaters to maintain one of T1 or T2 within a chosen range of Tc2 for a time t2, wherein t1 and t2 are both greater than or substantially equal to the minimum heating time tmin.

15. A heater device to heat a fluid container separable from the heater device comprising:

one or more substrates each forming a surface of a receiving location for the fluid container, a first heater disposed on a surface of a substrate in thermal communication with a first heat transfer surface within the receiving location, a second heater disposed on a surface of a substrate in thermal communication with a second heat transfer surface within the receiving location spaced apart from the first heat transfer surface, a first temperature sensor in thermal communication with the first heater, a second temperature sensor in thermal communication with the second heater, and a control means adapted to control the first heater using data from the first temperature sensor and to control the second heater using data from the second temperature sensor, each heater being controlled independently of the other, wherein the receiving location is configured to conform to the fluid container such that the first and the second heat transfer surfaces come into contact with the fluid container;

wherein the device is adapted to carry out a thermocycling reaction within the fluid chamber, the control means being configured to:

derive temperature relationship data relating Tr to one or both of T1 and T2 as described herein, control one or both of the first and the second heaters to heat the fluid chamber while receiving data from the first and the second temperature sensors, and use the temperature relationship data together with values of T1 and/or T2 to:

control the first and the second heaters to maintain Tr within a chosen range of a first control temperature Tc1 for a first time t1, and control the first and the second heaters to maintain Tr within a chosen range of a second control temperature Tc2 for a second time t2.

16. A method for heating a fluid container using a heater device, wherein the heater device comprises:

one or more substrates each forming a surface of a receiving location for the fluid container, a first heater disposed on a surface of a substrate in thermal communication with a first heat transfer surface within the receiving location, a second heater disposed on a surface of a substrate in thermal communication with a second heat transfer surface within the receiving location spaced apart from the first heat transfer surface, a first temperature sensor in thermal communication with the first heater, and a second temperature sensor in thermal communication with the second heater, wherein the receiving location is configured to conform to the fluid container such that the first and the second heat transfer surfaces come into contact with the fluid container, wherein the method comprises:

(i) heating the fluid container using both the first and the second heaters, (ii) receiving data from the first temperature sensor and using the data to control at least the first heater, and deriving a minimum heating time tmin following a change of heater power of the first or the second heater after which a temperature Tr within the fluid chamber is within a chosen range of one of T1 and T2.

17. A method according to claim 16 further comprising the step of alerting a user if an entered value of one of t1 and t2 are less than tmin.

18. A method for heating a fluid container using a heater device, wherein the heating device forms part of a thermocycler, wherein the heater device comprises:

one or more substrates each forming a surface of a receiving location for the fluid container, a first heater disposed on a surface of a substrate in thermal communication with a first heat transfer surface within the receiving location, a second heater disposed on a surface of a substrate in thermal communication with a second heat transfer surface within the receiving location spaced apart from the first heat transfer surface, a first temperature sensor in thermal communication with the first heater, and a second temperature sensor in thermal communication with the second heater, wherein the receiving location is configured to conform to the fluid container such that the first and the second heat transfer surfaces come into contact with the fluid container, wherein the method comprises:

(i) heating the fluid container using both the first and the second heaters, (ii) receiving data from the first temperature sensor and using the data to control at least the first heater, (iii) controlling the first and the second heaters to maintain Tr within a chosen range of a first control temperature Tc1 for a first time t1, (iv) controlling the first and the second heaters to maintain Tr within a chosen range of a second control temperature Tc2 for a second time t2, and (v) repeating the above steps (iii) and (iv) as part of a plurality of cycles of steps in the method.

19. A method according to claim 18 further comprising the step of setting one of t1 and t2 such that they are greater than or equal to tmin.

* * * * *